United States Patent
Thomas et al.

[11] Patent Number: 5,223,483
[45] Date of Patent: Jun. 29, 1993

[54] CYSTEINE-MODIFIED ACIDIC FIBROBLAST GROWTH FACTOR

[75] Inventors: Kenneth A. Thomas, Chatham Burough; David L. Linemeyer, Westfield, both of N.J.

[73] Assignee: Merck & Co., Inc., Rahway, N.J.

[21] Appl. No.: 938,310

[22] Filed: Aug. 28, 1992

Related U.S. Application Data

[63] Continuation of Ser. No. 759,128, Sep. 10, 1991, abandoned, which is a continuation of Ser. No. 244,431, Sep. 16, 1988, abandoned, which is a continuation-in-part of Ser. No. 112,600, Oct. 22, 1987, abandoned.

[51] Int. Cl.⁵ .................. A61K 37/36; C07K 13/00
[52] U.S. Cl. .................................. 514/12; 514/2; 530/399; 435/69.4; 435/172.3
[58] Field of Search .............. 514/12; 530/399; 435/69.4, 172.1, 172.3

[56] References Cited

U.S. PATENT DOCUMENTS 4,752,585  6/1988  Koths et al. ............... 435/256
4,835,260  5/1989  Shoemaker et al. ........ 530/397

FOREIGN PATENT DOCUMENTS 298723  1/1989  European Pat. Off. .

Primary Examiner—Robert A. Wax
Assistant Examiner—R. Keith Baker
Attorney, Agent, or Firm—John W. Wallen; Jack L. Tribble; Ray M. Speer

[57] ABSTRACT

Mutant human acidic fibroblast growth factor proteins are recombinantly produced having replaced cysteine residues with amino acids incapable of disulfide bond formation. The recombinantly produced mutant human acidic fibroblast growth factor proteins have improved biological activity in the absence of heparin when compared to wild-type recombinant human acidic fibroblast growth factor.

22 Claims, 2 Drawing Sheets

CYSTEINE-MODIFIED ACIDIC FIBROBLAST GROWTH FACTOR

RELATED U.S. APPLICATION DATA

This application is a continuation of Ser. No. 07/759,128, filed Sep. 10, 1991, now abandoned, which is a continuation of application Ser. No. 07/244,431, filed Sep. 16, 1988, now abandoned, which is a continuation-in-part application of Ser No. 07/112,600, filed Oct. 22, 1987, now abandoned.

BACKGROUND OF THE INVENTION

The discovery of substances that control the growth of animal cells, especially human cells, and the mechanism by which they work is currently one of the major focuses of biomedical research concerned with tissue repair and wound healing. Fibroblast growth factors (FGFs), mitogens for various cell types including many cells of mesodermal origin, have been identified and it has been suggested that they may induce mitosis which will result in tissue repair. Fibroblast mitogenic activity was first observed with extracts of tissue from the central nevous system. Brain-derived fibroblast mitogens were first described by Trowell et al., J. Exp. Biol. 16: 60-70 (1939) and Hoffman, Growth 4: 361-376 (1940). It was subsequently shown that pituitary extracts also had potent mitogenic activity for fibroblastoid cells, Amelin, Proc. Natl. Acad. Sci. USA 70: 2702-2706 (1973). Partial purification of both brain and pituitary fibroblast growth factor revealed mitogenic activity for a variety of cell types of differentiated cells including vascular endothelial cells, Gospodarowicz et al., Natl. Cancer Inst. Monogr. 48: 109-130 (1978). Fibroblast growth factor was originally thought to be a single peptide derived from the limited proteolysis of myelin basic protein. It has recently been shown that FGF exists in two forms, acidic FGF (aFGF) and basic FGF (bFGF), and both forms can be isolated and purified from mammalian brain, Thomas and Gimenez-Gallego, TIBS 11: 81-84 (1986). Numerous cell types respond to stimulation with either purified aFGF or bFGF to synthesize DNA and divide, including primary fibroblasts, vascular and corneal endothelial cells, chondrocytes, osteoblasts, myoblasts, smooth muscle, glial cells and neuroblasts, Esch et al., Proc. Natl. Acad. Sci. USA 82: 6507-6511 (1985); Kuo et al., Fed. Proc. 44: 695 (1985); Gensburger et al., C.R. Acad. Sc. Paris 303: 465-468 (1986). Pure bovine brain-derived aFGF not only acts as a potent mitogen for vascular endothelial cells in culture but also induces blood vessel growth in vivo, Thomas, et al. Proc. Acad. Sci. USA 82: 6409-6413 (1985). The mitogenic activity of purified aFGF can also be used to promote wound healing, Thomas, U.S. Pat. No. 4,444,760.

Acidic fibroblast growth factor was originally purified to homogeneity from bovine brain based on its mitogenic activity for BALB/c 3T3 fibroblasts, Thomas et al., Proc. Natl. Acad. Sci. USA 81: 357-361 (1984). This brain-derived growth factor has been repurified and renamed in multiple laboratories based both on its: mitogenic activity for vascular endothelial and astroglial cells (endothelial cell growth factor and astroglial growth factor 1), source (retinal derived growth factor, eye derived growth factor II, and perhaps brain derived growth factor), and binding to heparin Sepharose (class 1 heparin-binding growth factor or heparin-binding growth factor alpha), Thomas and Gimenez-Gallego TIBS 11: 81-84 (1986). The amino acid sequence of bovine aFGF has been determined, recognized to be highly homologous to basic FGF and related to the fibroblast mitogens interleukin 1-alpha and 1-beta, Gimenez-Gallego et al., Science 230: 1385-1388 (1985). The complete amino acid sequence of human aFGF has been determined from the purified protein, Gimenez-Gallego et al., Biochem. Biophy. Res. Comm. 138: 611-617 (1986, and from the gene, Jaye et al., Science 233: 541-545 (1986).

Native aFGF purified from brain or recombinant derived aFGF (r-aFGF) requires the co-administration of heparin to optimally stimulate Balb/c 3T3 fibroblasts and vascular endothelial cells in culture. Human brain derived and recombinant aFGF are only about.1% to 5% as active on these cells in culture in the absence of heparin compared to optimal activity in the presence of heparin. While the doses required for maximal aFGF activity are relatively low, it might be desirable to administer aFGF with no heparin since heparin could conceivably elicit detrimental side effects. Pure human aFGF, in addition to the standard conditions that destroy the activity of most proteins, extremes of heat, pH and the presence of proteases, is also labile to lyophilization and oxidation. The pure aFGF becomes cross-linked through intrachain or interchain disulfide bonds by oxidation and can be recovered in active form by disulfide reduction with 20 mM dithiothreitol. Heparin can inhibit intermolecular disulfide bond mediated aggregation of aFGF. This heterogeneous glycosaminoglycan has also been noted to stabilize aFGF from heat denaturation and proteolytic degradation by trypsin. Consequently, either exogenous or endogenous heparin is required for the in vivo activity associated with tissue repair. The present invention provides unique mutated forms of recombinant-derived aFGF which have an increased biological activity in the absence of heparin compared to native aFGF.

OBJECT OF THE INVENTION

It is, accordingly, an object of the present invention to convert by mutation recombinant bovine and human aFGF genes to genes capable of encoding proteins which are more active in the absence of heparin than the native or recombinant protein. Another object is to incorporate the specific genes into appropriate cloning vectors. A further object is to transform an appropriate host with each of the recombinant vectors and to induce expression of the specific mutated aFGF genes. Another object is to isolate and purify biologically active bovine and human mutated aFGF. These and other objects of the present invention will be apparent from the following description.

SUMMARY OF THE INVENTION

Novel genes coding for mutated bovine and human aFGF are constructed. The unique genes are derived from genes encoding recombinant native bovine and human aFGF by specific point mutation. Each gene construct is inserted into an expression vector which is used to transform an appropriate host. The transformed host cells produce unique mutated recombinant aFGF, human or bovine, which is purified and has enhanced or improved biological activity in the absence of heparin compared to the unmutated forms.

DETAILED DESCRIPTION

Figure 1:
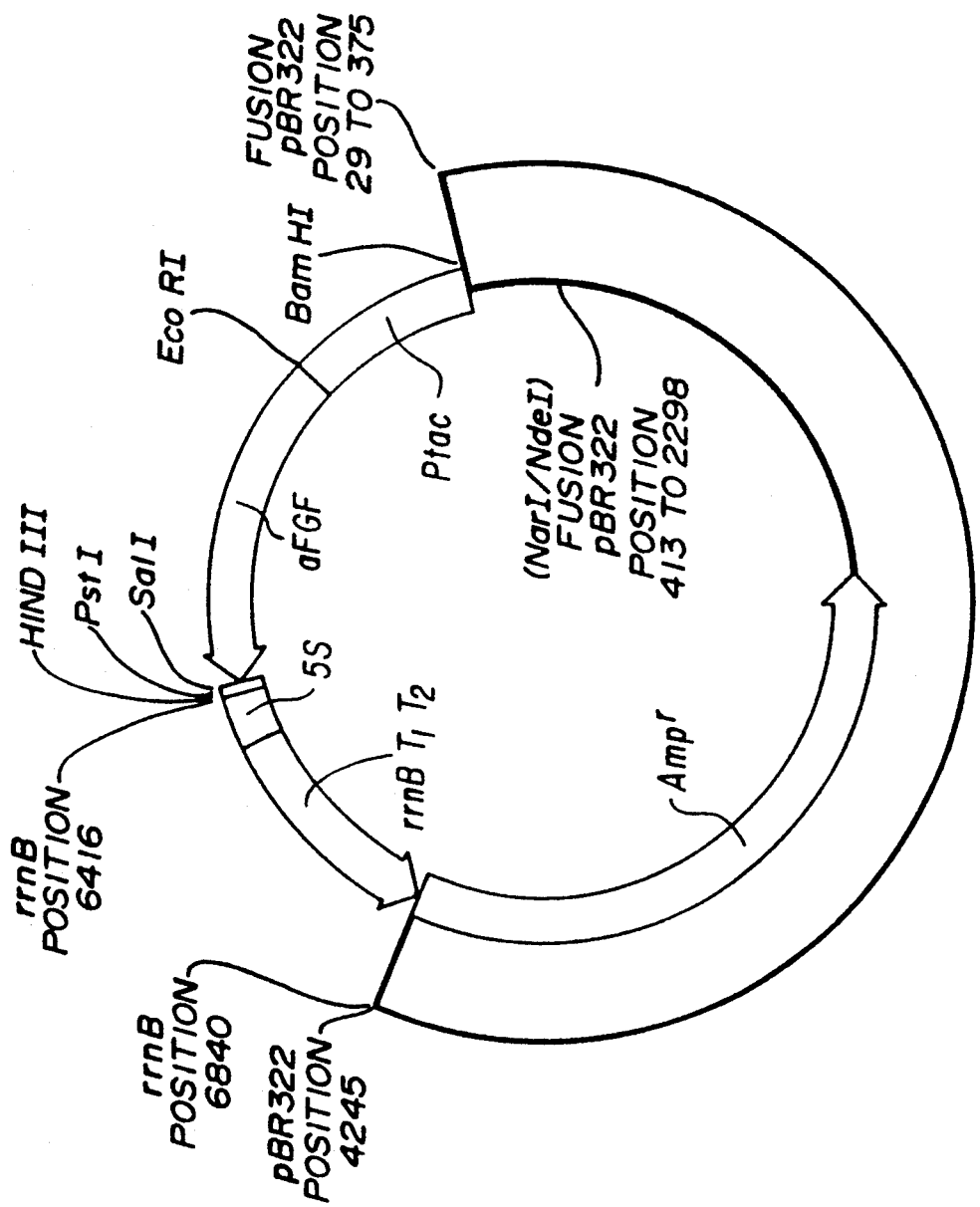
FIG. 1 is a diagram of the pKK223-3 plasmid containing a gene for mutant r-aFGF.

Acidic fibroblast growth factor exists in various microheterogeneous forms which are isolated from the various tissue sources and cell types known to contain aFGF. Microheterogeneous forms as used herein refer to a single gene product, that is a protein produced from a single gene unit of DNA, which is structurally modified following translation. These structural modifications, however, do not result in any significant alterations of biological activity of the peptide Biological activity and biologically active are used interchangably and are herein defined as the ability of native, recombinant or mutant recombinant aFGF to stimulate DNA synthesis in quiescent Balb/c 3T3 fibroblasts as described in Example 7, to stimulate any of the cell types described above or to carry out any of the functions described in the art. The modifications may take place either in vivo or during the isolation and purification process. In vivo modification results in, but is not limited to, acetylation at the N-terminus, proteolysis, qlycosylation or phosphorylation. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in the production of microheterogeneous forms. The most common modification occuring during purification is proteolysis which is generally held to a minimum by the use of protease inhibitors. Under most conditions a mixture of microheterogeneous forms are present following purification of native aFGF. Native aFGF refers to aFGF isolated and purified from tissues or cells that contain aFGF.

The invention is contemplated to include all animal microheterogeneous forms of acidic fibroblast growth factor. The preferred embodiments include bovine and human microheterogeneous forms of aFGF. The most preferred microheterogeneous forms of bovine aFGF include a 154 amino acid form, a 140 amino acid form and a 134 amino acid form. The 140 amino acid form is shown in Table I, Gimenez-Gallego et al., Science 230: 1385-1388 (1985), and is the most preferred of the bovine species.

TABLE I

Amino Acid Sequence of Bovine aFGF 1  10  20
PheAsnLeuProLeuGlyAsnTyrLysLysProLysLeuLeuTyrCysSerAsnGlyGlyTyrPheLeuArgIleLeu 30  40  50
ProAspGlyThrValAspGlyThrLysAspArgSerAspGlnHisIleGlnLeuGlnLeuCysAlaGluSerIleGlyGlu 60  70  80
ValTyrIleLysSerThrGluThrGlyGlnPheLeuAlaMetAspThrAspGlyLeuLeuTyrGlySerGlnThrProAsn 90  100
GluGluCysLeuPheLeuGluArgLeuGluGluAsnHisTyrAsnThrTyrIleSerLysLysHisAlaGluLysHisTrp 110  120
PheValGlyLeuLysLysAsnGlyArgSerLysLeuGlyProArgThrHisPheGlyGlnLysAlaIleLeuPheLeuPro 140
LeuProValSerSerAsp The nucleotide sequence of the 140 amino acid form, recombinant, of bovine aFGF is shown in Table II.

TABLE II

Nucleotide Sequence of Bovine aFGF 1  20  40  60
AATTCATGTTCAATCTGCCACTGGGTAATTACAAAAAGCCAAAGCTTCTTTACTGCTCTAA
GTACAAGTTAGACGGTGACCCATTAATGTTTTTCGGTTTCGAAGAAATGACGAGATT

80
CGGTGGTTACTTTCTCCGC
GCCACCAATGAAAGAGGCG 100  120  140
ATCCTGCCAGATGGTACCGTGGACGGCACCAAAGATCGTTCTGATCAACATATTCAACTGC
TAGGACGGTCTACCATGGCACCTGCCGTGGTTTCTAGCAAGACTAGTTGTATAAGTTGACG

160
AGCTGTGCGCCGAATCTAT
TCGACACGCGGCTTAGATA 180  200  220
CGGTGAAGTTTACATCAAATCTACCGAAACTGGTCAATTCCTTGCCATGGACACTGATGGC
GCCACTTCAAATGTAGTTTAGATGGCTTTGACCAGTTAAGGAACGGTACCTGTGACTACCG

TABLE II-continued

Nucleotide Sequence of Bovine aFGF

```
                                                                          240
                                                    CTGCTGTACGGATCCCAGA
                                                    GACGACATGCCTAGGGTCT 260                    280                          300
CCCCAAACGAGGAGTGCCTTTTCCTGGAGCGCCTGGAGGAAAACCATTACAACACCTACAT
GGGGTTTGCTCCTCACGGAAAAGGACCTCGCGGACCTCCTTTTGGTAATGTTGTGGATGTA

320
                                                    CTCTAAAAAGCATGCTGAG
                                                    GAGATTTTCGTACGACTC 340                    360                          380
AAACATTGGTTCGTAGGCCTTAAGAAAAATGGCCGCTCTAAACTGGGCCCTCGTACTCACT
TTTGTAACCAAGCATCCGGAATTCTTTTTACCGGCGAGATTTGACCCGGGAGCATGAGTGA

400
                                                    TTGGTCAAAAAGCTATCCT
                                                    AACCAGTTTTTCGATAGGA 420                    440
GTTCCTGCCACTGCCAGTGAGCTCTGACTAATAGATATCG
CAAGGACGGTGACGGTCACTCGAGACTGATTATCTATAGCAGCT
```

The 154 amino acid form includes the following additional amino acids; Ala-Glu-Gly-Glu-Thr-Thr-Thr-Phe-Thr-Ala-Leu-Thr-Glu-Lys, with the carboxyl terminus Lys attached to the amino terminus Phe at the first position of the 140 amino acid form. The amino terminal alanine residue of the 154 amino acid form of the bovine aFGF may be acetylated. The 134 amino acid form is identical to the 140 amino acid form except that the first 6 amino acids of the amino terminus have been removed. When native aFGF is isolated the relative amounts of these microheterogeneous forms vary depending on the process used but generally contain at least two of these forms.

Human aFGF exhibits a similar microheterogeneity to that of bovine aFGF. The most preferred microheterogeneous forms of human aFGF include a 154 amino acid form, a 140 amino acid form and a 139 amino acid form. The human 140 amino acid form differs from the bovine form by eleven amino acids, as shown in TABLE VIII. The 154 amino acid form contains the exact sequence of the human 140 amino acid form plus the 14 additional amino acids associated with the bovine 154 amino acid form, with one exception. The amino acid at the fifth position of the N-terminus or at the -10 position as determined from the 140 amino acid Phe N-terminus in the human form is isoleucine and is substituted for the threonine in the bovine form. The additional 14 amino acid human N-terminal sequence is; Ala-Glu-Gly-Glu Ile-Thr-Thr-Phe-Thr-Ala-Leu-Thr-Glu-Lys. The additional amino acids of the 154 amino acid form are numbered from the N-terminal Ala, -14, to the carboxyl terminal Lys,-1. The amino terminal alanine residue at the -14 position may be acetylated. A third form of human aFGF contains 139 amino acids and is equivalent to the human 140 amino acid form with the amino terminal phenylalanine residue removed. The amino terminal asparagine residue may be deamidated to aspartic acid in the 139 amino acid form of human aFGF. The 140 and 139 amino acid forms are the most preferred forms of the human microheterogeneous forms. The 140 amino acid form is shown in Table III, Gimenez-Gallego et al., Biochem. Giophys, Res. Comm. 138: 611–617 (1986).

TABLE III

Amino Acid Sequence of Human aFGF

```
    1                              10                             20
PheAsnLeuProProGlyAsnTyrLysLysProLysLeuLeuTyrCysSerAsnGlyGlyHisPheLeuArgIleLeu 30                             40                             50
ProAspGlyThrValAspGlyThrArgAspArgSerAspGlnHisIleGlnLeuGlnLeuSerAlaGluSerValGlyGlu 60                             70                             80
ValTyrIleLysSerThrGluThrGlyGlnTyrLeuAlaMetAspThrAspGlyLeuLeuTyrGlySerGlnThrProAsn 90                            100
GluGluCysLeuPheLeuGluArgLeuGluGluAsnHisTyrAsnThrTyrIleSerLysLysHisAlaGluLysAsnTrp 110                           120
PheValGlyLeuLysLysAsnGlySerCysLysArgGlyProArgThrHisTyrGlyGlnLysAlaIleLeuPheLeuPro

140
LeuProValSerSerAsp
```

The nucleotide sequence of the 140 amino acid form, recombinant, of human aFGF is shown in Table IV.

TABLE IV

Nucleotide Sequence of Bovine aFGF

```
1                    20                       40                       60
AAT TCA TGT TCA ATC TGC CAC CGG GTA ATT ACA AAA AGC CAA AGC TTC TTT TAC TGC TCT AA
    GTA CAA GTT AGA CGG TGG CCC ATT AAT GTT TTT CGG TTT CGA AGA AAT GAC GAG ATT

80
                                                CGG TGG TCA CTT TCT CCG C
                                                GCC ACC AGT GAA AGA GGC G 100                     120                      140
AT CCT GCC AGA TGG TAC CGT GGA CGG CAC CAG AGA TCG TTC TGA TCA ACA TAT TCA ACT GC
TA GGA CGG TCT ACC ATG GCA CCT GCC GTG GTC TCT AGC AAG ACT AGT TGT ATA AGT TGA CG

160
                                                AGC TGT CCG CCG AAT CTG T
                                                TCG ACA GGC GGC TTA GAC A 180                      200                       220
CGG TGA AGT TTA CAT CAA ATC TAC CGA AAC TGG TCA ATA CCT TGC CAT GGA CAC TGA TGG C
GCC ACT TCA AAT GTA GTT TAG ATG GCT TTG ACC AGT TAT GGA ACG GTA CCT GTG ACT ACC G

240
                                                CT GCT GTA CGG ATC CCA GA
                                                GA CGA CAT GCC TAG GGT CT 260                      280                     300
CCC CAA ACG AGG AGT GCC TTT TCC TGG AGC GCC TGG AGG AAA ACC ATT ACA ACA CCT ACA T
GGG GTT TGC TCC TCA CGG AAA AGG ACC TCG CGG ACC TCC TTT TGG TAA TGT TGT GGA TGT A

320
                                                CTC TAA AAA GCA TGC TGA G
                                                GAG ATT TTT CGT ACG ACT C 340                      360                      380
AAA AAT TGG TTC GTA GGC CTT AAG AAA AAT GGC AGC TGT AAA CGC GGC CCT CGT ACT CAC T
TTT TTA ACC AAG CAT CCG GAA TTC TTT TTA CCG TCG ACA TTT GCG CCG GGA GCA TGA GTG A

400
                                                AT GGC CAA AAA GCT ATC CT
                                                TA CCG GTT TTT CGA TAG GA 420                     440
GTT CCT GCC ACT GCC AGT GAG CTC TGA CTA ATA GAT ATC G
CAA GGA CGG TGA CGG TCA CTC GAG ACT GAT TAT CTA TAG CAG CT
```

The preferred procedure for obtaining a gene for mammalian aFGF is to synthesize the gene because this allows optimization of translated protein and ease of mutagenesis. The gene may be synthesized based on the amino acid sequence of a microheterogeneous form of aFGF obtained from any animal including man. The preferred method is to use the bovine amino acid sequence for aFGF and chemically point mutate the base sequence, to produce the genes for other species, Linemeyer et al. Biotechnol. 5:960-965 (1987).

The synthetic genes are based on the determined bovine amino acid sequence described by Gimenez-Gallego et al., Science 230: 1385-1388 (1985) and the human amino acid sequence as described by Gimenez-Gallego et al. Biochem. Biophys. Res. Comm., 138: 611-617 (1986) and shown in Tables I and III. The unique nucleotide sequence of the 140 amino acid form of bovine aFGF is derived from reverse translation of the amino acid sequence by a technique similar to that of Itakura et al., Science 198: 1056-1063 (1977). The various novel nucleotide sequences corresponding to the native amino acid sequence of bovine aFGF are shown in the following table:

TABLE V

```
                           5                            10                          15                         20
Phe  Asn  Leu  Pro  Leu  Gly  Asn  Tyr  Lys  Lys  Pro  Lys  Leu  Leu  Tyr  Cys  Ser  Asn  Gly  Gly
TTQ  AAQ  CTN  CCN  CTN  GGN  AAQ  TAQ  AAP  AAP  CCN  AAP  CTN  CTN  TAQ  TGQ  TCN  AAQ  GGN  GGN
          TTP       TTP                                          TTP  TTP            AGQ 25                           30                          35                         40
Tyr  Phe  Leu  Arg  Ile  Leu  Pro  Asp  Gly  Thr  Val  Asp  Gly  Thr  Lys  Asp  Arg  Ser  Asp  Gln
TAQ  TTQ  CTN  CGN  ATQ  CTN  CCN  GAQ  GGN  ACN  GTN  GAQ  GGN  ACN  AAP  GAQ  CGN  TCN  GAQ  CAP
          TTP  AGP  ATA  TTP                                                       AGP  AGQ 45                           50                          55                         60
His  Ile  Gln  Leu  Gln  Leu  Cys  Ala  Glu  Ser  Ile  Gly  Glu  Val  Tyr  Ile  Lys  Ser  Thr  Glu
CAQ  ATQ  CAP  CTN  CAP  CTN  TGQ  GCN  GAP  TCN  ATQ  GGN  GAP  GTN  TAQ  ATQ  AAP  TCN  ACN  GAP
     ATA       TTP       TTP                      AGQ  ATA                 ATA       AGQ 65                           70                          75                         80
Thr  Gly  Gln  Phe  Leu  Ala  Met  Asp  Thr  Asp  Gly  Leu  Leu  Tyr  Gly  Ser  Gln  Thr  Pro  Asn
ACN  GGN  CAP  TTQ  CTN  GCN  ATG  GAQ  ACN  GAQ  GGN  CTN  CTN  TAQ  GGN  TCN  CAP  ACN  CCN  AAQ
               TTP                                          TTP  TTP            AGQ
```

TABLE V-continued

|     |     |     |     | 85  |     |     |     |     | 90  |     |     |     |     | 95  |     |     |     |     | 100 |
|-----|-----|-----|-----|-----|-----|-----|-----|-----|-----|-----|-----|-----|-----|-----|-----|-----|-----|-----|-----|
| Glu | Glu | Cys | Leu | Phe | Leu | Glu | Arg | Leu | Glu | Glu | Asn | His | Tyr | Asn | Thr | Tyr | Ile | Ser | Lys |
| GAP | GAP | TGQ | CTN | TTQ | CTN | GAP | CGN | CTN | GAP | GAP | AAQ | CAQ | TAQ | AAQ | ACN | TAQ | ATQ | TCN | AAP |
|     |     |     | TTP |     | TTP |     | AGP | TTP |     |     |     |     |     |     |     |     | ATA | AGQ |     |

|     |     |     |     | 105 |     |     |     |     | 110 |     |     |     |     | 115 |     |     |     |     | 120 |
|-----|-----|-----|-----|-----|-----|-----|-----|-----|-----|-----|-----|-----|-----|-----|-----|-----|-----|-----|-----|
| Lys | His | Ala | Glu | Lys | His | Trp | Phe | Val | Gly | Leu | Lys | Lys | Asn | Gly | Arg | Ser | Lys | Leu | Gly |
| AAP | CAQ | GCN | GAP | AAP | CAQ | TGG | TTQ | GTN | GGN | CTN | AAP | AAP | AAQ | GGN | CGN | TCN | AAP | CTN | GGN |
|     |     |     |     |     |     |     |     |     |     | TTP |     |     |     |     | AGP | AGQ |     | TTP |     |

|     |     |     |     | 125 |     |     |     |     | 130 |     |     |     |     | 135 |     |     |     |     | 140 |
|-----|-----|-----|-----|-----|-----|-----|-----|-----|-----|-----|-----|-----|-----|-----|-----|-----|-----|-----|-----|
| Pro | Arg | Thr | His | Phe | Gly | Gln | Lys | Ala | Ile | Leu | Phe | Leu | Pro | Leu | Pro | Val | Ser | Ser | Asp |
| CCN | CGN | ACN | CAQ | TTQ | GGN | CAP | AAP | GCN | ATQ | CTN | TTQ | CTN | CCN | CTN | CCN | GTN | TCN | TCN | GAQ |
|     | AGP |     |     |     |     |     |     |     | ATA | TTP |     | TTP |     | TTP |     |     | AGQ | AGQ |     |

Where Q = C or T,
P = A or G, and
N = A, T, C, or G

The bovine gene is constructed with a leader portion containing a single restriction enzyme cleavage site and an N-terminal methionine codon for a translational start site. The gene also contains a tail containing tandem translational stop codons and two restriction enzyme cleavage sites. The redundancy of the genetic code allows a choice of base sequences which in turn allows for the incorporation of unique restriction enzyme cleavage sites throughout the gene. The preferred bovine gene base sequence with the location of the restriction enzyme cleavage sites is shown in the following table:

TABLE VI

```
  1                  10                    20                    30
  MetPheAsnLeuProLeuGlyAsnTyrLysLysProLysLeuLeuTyrCysSerAsnGlyGlyTrpPheLeuArgIleLeuProAspGlyThrValAspGlyThrLysAspArgSer
                                  [1]                                                                        [3]
                    20                    40                    60                    80
AATTCATGTTCAATCTGCCACTGGGTAATTACAAAAAGCCAAAGCTTCTTTACTGCTCTAACGGTGGTTACTTTCTCCGCATCCTGCCAGATGGT
GTACAAGTTAGACGGTGACCCATTAATGTTTTTCGGTTTCGAAGAAATGACGAGATTGCCACCAATGAAAGAGGCGTAGGACGGTCTACCA
      [2]                                                                                                   [4]
                                                                                         100                    120
                                                                            ACCGTGGACGGCACCAAAGATCGTTCT
                                                                            TGGCACCTGCCGTGGTTTCTAGCAAGA
(EcoRI)                                           HindIII                                         KpnI 40                    50                    60                    70
  AspGlnHisIleGlnLeuCysAlaGluIleGlySerIleGlyGluValTyrIleLysSerThrGluThrGlyGlnPheLeuAlaMetAspThrAspGlyLeuLeuTyrGlySerGlnThr
                                                                         [7]
                    140                    160                    180                    200
GATCAACATATTCAACTGCAGCTGTGCGCCGAATCTATCGGTGAAGTTTACATCAAATCTACCGAAACTGGTCAATTCCTTGCCATGGACACT
CTAGTTGTATAAGTTGACGTCGACACGCGGCTTAGATAGCCACTTCAAATGAGTTTAGATGGCTTTGACCAGTTAAGGAACGGTACCTGTGA
      [6]                                                                  [8]
  Bcl        PstIPvuII        HinfI                                                                          NcoI 220                    240
                                                                         GATGGCCTGCTGTACGGATCCCAGACC
                                                                         CTACCGGACGACATGCCTAGGGTCTGG
                                                                                                         BamHI 80                    90                    100                    110
  ProAsnGluGluArgLeuGluGluAsnHisTyrAsnThrTyrIleSerLysLysHisAlaGluHisTrpPheValGlyLeuLysLysAsnGlyArgSerLys
                                       [9]                                             [11]
                    260                    280                    300                    320
CCAAACGAGAGTGCCTTTTCCTGGAGCGCCTCGGCGAACCTCGCGGACCTCCTTTGGTAATGTTTGTGGATGTAGAGATTTTTCGTACGACTCTTTGTAACCAA
GGTTTGCTCTCACGGGAAAGGACCTCGCGGAGCCGCTTGGAGAAACATTACAAACACCTACATCTCTAAAAAGCATGCTGACTGAGAAACATTGGTT
                                       [10]
                               HaeII                                                                     SphI 340                    360
                                                                         CGTAGGCCTTAAGAAAAATGGCCGCTCTAAA
                                                                         GCATCCGGAATTCTTTTTACCGGCGAGATTT
                                                                                            StuI 120                    130                    140
  LeuGlyProArgThrHisPheGlyGlnLysAlaIleLeuPheLeuProValSerSerAsp...
          [13]
                    380                    400                    420                    440
CTGGGCCCTCGTACTCACTTTGGTCAAAAAGCTATCCTGTTCCTGCCACTGCCAGTGAGCTCTGACTAATAGATATCG
GACCCGGGAGCATGAGTGAAACCAGTTTTTCGATAGGACAAGGACGGTCACTCGAGACTGATTATCTATAGCAGCT
      ApaI                                                        [16]
                                                        [15]
                                                                SacI        EcoRV (SalI)
```

The gene sequence for each strand of the double-stranded molecule is randomly divided into 8 nucleotide sequences. The oligonucleotides are constructed with overlapping ends to allow the formation of the double-stranded DNA. The following table contains one of a multitude of oligonucleotide arrangements that is used to produce the bovine aFGF gene.

TABLE VII

| | 10 | 20 | 30 | 40 | 50 | 60 | |
|---|---|---|---|---|---|---|---|
| OLIGO-1 5' | AATTCATGTT | CAATCTGCCA | CTGGGTAATT | ACAAAAAGCC | AAAGCTTCTT | TACTGCTC | 58 3' |
| OLIGO-2 5' | AGAAGCTTTG | GCTTTTTGTA | ATTACCCAGT | GGCAGATTGA | ACATG | | 45 3' |
| OLIGO-3 5' | TAACGGTGGT | TACTTTCTCC | GCATCCTGCC | AGATGGTACC | GTGGACGGCA | CCAAAGATCG | 60 3' |
| OLIGO-4 5' | TGCCGTCCAC | GGTACCATCT | GGCAGGATGC | GGAGAAAGTA | ACCACCGTTA | GAGCAGTAA | 59 3' |
| OLIGO-5 5' | TTCTGATCAA | CATATTCAAC | TGCAGCTGTG | CGCCGAATCT | ATCGGT | | 46 3' |
| OLIGO-6 5' | GTAAACTTCA | CCGATAGATT | CGGCGCACAG | CTGCAGTTGA | ATATGTTGAT | CAGAACGATC | 60 3' |
|  |  |  |  |  |  | TTTGG | 65 3' |
| OLIGO-7 5' | GAAGTTTACA | TCAAATCTAC | CGAAACTGGT | CAATTCCTTG | CCATGGACAC | TGATGGCCTG | 60 3' |
|  |  |  |  |  |  | CTGTACG | 67 3' |
| OLIGO-8 5' | GATCCGTACA | GCAGGCCATC | AGTGTCCATG | GCAAGGAATT | GACCAGTTTC | GGTAGATTTG | 60 3' |
|  |  |  |  |  |  | AT | 62 3' |
| OLIGO-9 5' | GATCCCAGAC | CCCAAACGAG | GAGTGCCTTT | TCCTGGAGCG | CCTGGAGGAA | | 50 3' |
|  |  |  |  |  | AA | | 52 3' |
| OLIGO-10 5' | GGTGTAATGG | TTTTCCTCCA | GGCGCTCCAG | GAAAAGGCAC | TCCTCGTTTG | GGGTCTGG | 58 3' |
| OLIGO-11 5' | CCATTACAAC | ACCTACATCT | CTAAAAAGCA | TGCTGAGAAA | CATTGGTT | | 48 3' |
| OLIGO-12 5' | GGCCTACGAA | CCAATGTTTC | TCAGCATGCT | TTTTAGAGAT | GTAGGT | | 46 3' |
| OLIGO-13 5' | CGTAGGCCTT | AAGAAAAATG | GCCGCTCTAA | ACTGGGCCCT | CGTACTCACAT | TTG | 53 3' |
| OLIGO-14 5' | GCTTTTTGAC | CAAAGTGAGT | ACGAGGGCCC | AGTTTAGAGC | GGCCATTTTT | CTTAA | 55 3' |
| OLIGO-15 5' | GTCAAAAAGC | TATCCTGTTC | CTGCCACTGC | CAGTGAGCTC | TGACTAATAG | ATATCG | 56 3' |
| OLIGO-16 5' | TCGACGATAT | CTATTAGTCA | GAGCTCACTG | GCAGTGGCAG | GAACAGGATA | | 50 3' |

The oligonucleotides illustrated in Table VII are presented merely as an example of oligonucleotide subunits and should not be construed as limiting thereto. The composite base sequence showing the overlap and arrangement of the oligonucleotides is illustrated in Table II.

The bovine gene is assembled in 2 steps: first, the half corresponding to the N-terminal portion of the protein; and second, the C-terminal half. Generally, the oligonucleotides are kinased with T4 polynucleotide kinase in the presence of either ATP or $^{32}P$ labelled ATP. In the first reaction of each step the oligonucleotides which make up one strand of the gene are kinased with the exception of the most 5' oligonucleotide. In the second reaction the oligonucleotides which make up the second strand are kinased, with the exception of the most 5' oligonucleotide. When kinased oligonucleotides are used, about 1% of the added oligonucleotide is $^{32}P$-labelled for later identification of the products. Annealing is carried out in an appropriate buffer, such as one containing but not limited to about 60 mM TRIS, about pH 7.6, about 5 mM dithiothreitol (DTT), about 10 mM $MgCl_2$, and about 30 μM ATP at about 90° C. for about 4 minutes followed by a rapid transfer to about 60° C. and a slow cooling to about 30° C. Ligation is carried out in an appropriate buffer, such as one containing, but not limited to, about 60 mM TRIS, about pH 7.6, about 10 mM DTT, about 10 mM $MgCl_2$, about 1 mM ATP, and about 0.03 units T4 DNA ligase at about 20° C. for about 1 and ½ hour.

The ligated oligonucleotides are purified by polyacrylamide gel electrophoresis following ethanol precipitation. The oligonucleotides are redissolved in a buffer containing about 20 μl of about 80% formamide, about 50 mM TRIS borate, about pH 8.3, about 1 mM ethylenediaminetetraacetic acid (EDTA), about 0.1% (w/v) xylene cyanol, and about 0.1% (w/v) bromophenol blue. Each sample is heated at about 90° C. for about 3 minutes and electrophoresed in about a 10% urea-polyacrylamide gel at about 75 watts for about 5 hours. The 231 base N-terminal bands are removed, combined and eluted at about 4° C. in about 0.5M ammonium acetate containing about 1 mM EDTA at about pH 8. The 209 base C-terminal bands are treated in the same manner.

The synthetic gene sequences coding for either the N-terminal or the C-terminal portions of the aFGF are incorporated into the pBR322 plasmid. It is especially desired and intended that there be included within the scope of this invention, the use of other plasmids into which the aFGF gene can be incorporated and which will allow the expression of the aFGF gene. Reannealed oligonucleotides, about 300 fmole and about 100 fmole of the recovered 231 base pair N-terminus are each ligated to about 100 fmole of agarose gel purified about 3.9 kilo base (kb) EcoRI-BamHI pBR322 for the N terminus. The 209 bp C-terminus is constructed in the same manner using BamHI-SalI pBR322. Ligation is carried out in a buffer containing about 25 mM TRIS, about pH 7.8, about 1 mM DTT, about 10 mM $MgCl_2$, about 0.4 mM ATP, with about 1 unit of T4 DNA ligase for about 1 hour at about 20° C. Each half gene ligated vector is used to transform competent bacterial cells, such as E. coli RR1 (Bethesda Research Laboratories, BRL) following suppliers procedures. The transformed cells are selected for growth in ampicillin and screened for the presence of either the 231 base pair (bp) EcoRI-BamHI insert or the 209 bp BamHI SalI insert by restriction analysis of mini lysate plasmid preparations.

The DNA sequence of clones containing the appropriate sized inserts is determined using Maxam and Gilbert, Proc. Natl. Acad. Sci. USA 74: 560–564 (1977) chemical DNA sequence techniques.

The final full-length aFGF synthetic gene was cloned by cleaving the N-terminal half clone with restriction enzymes BamHI and SalI, treating with alkaline phosphatase and ligating this to the gel purified 209 bp BamHI-SalI insert of the C-terminal half clone. This ligated material was used to transform competent RR1 cells as before.

Expression of the synthetic aFGF gene is accomplished by a number promoter-expression systems. It is desired and intended that there be included within the scope of this invention, the use of other promoter-expression systems for the expression of the intact aFGF gene. The preferred construct uses the E. coli tac promoter, a hybrid between regions of the trp promoter and the lac promoter as described by deBoer et al., Proc. Nat. Acad. Sci. USA 80: 21–25 (1983). Plasmid pKK223-3 (Pharmacia) which contains the tac promoter and rrnB rRNA transcription terminator was modified to remove the pBR322-derived SalI restriction enzyme site. The rrnB rRNA terminator has been shown to allow expression by strong promoters, Gentz et al., Proc. Natl. Acad. Sci. USA 78: 4936–4940 (1981); Brosius, Gene 27: 161–172 (1984).

The pKK223-3 plasmid DNA is cleaved with restriction enzymes to produce a 2.7 kb DNA fragment to generate clone pKK2.7. The synthetic aFGF gene is cleaved from its pBR322 vector and transferred to the pKK2.7 plasmid after restricting pKK2.7 with EcoRI and SalI. The resulting recombinant, shown in FIG. 1, is transformed into E. coli JM105 (Pharmacia) or DH5 (BRL) cells and expressed.

Site specific mutagenesis is an efficient way to convert the amino acid sequence of one mammalian species of aFGF to the aFGF amino acid sequence of another species. The following description relates to the site specific mutagenic conversion of bovine aFGF, 140 amino acid form (numbered in accordance with the native form), to human aFGF, it is to be understood, however, that the process can be used to convert any mammalian species aFGF to that of any other species. The only limitation on the conversion is that the amino acid sequences of both aFGFs must be known. The following table lists the amino acids which must be substituted and the location on the bovine aFGF amino acid map, Table VI, at which the substitutions are made:

TABLE VIII

| Amino Acid Location | Substituted Amino Acids | |
|---|---|---|
| | Human aFGF | for Bovine aFGF |
| 5 | Pro | Leu |
| 21 | His | Tyr |
| 35 | Arg | Lys |
| 47 | Ser | Cys |
| 51 | Val | Ile |
| 64 | Tyr | Phe |
| 106 | Asn | His |
| 116 | Ser | Arg |
| 117 | Cys | Ser |
| 119 | Arg | Leu |
| 125 | Tyr | Phe |

As with the bovine gene sequence eight oligonucleotides representing the human gene sequence are constructed by the same procedure as that used for the bovine oligonucleotides. The following table contains on of a multiple of oligonucleotide arrangements that is used to produce the human aFGF gene.

TABLE IX

OLIGO-1
5'  CTGCCACCGGGTAATTAC  3'

OLIGO-2
5'  CGGTGGTCACTTTCTCCG  3'

OLIGO-3
5'  CGGCACCAGAGATCGTTC  3'

OLIGO-4
5'  GCAGCTGTCCGCCGAATCTGTCGGTGAAG  3'

OLIGO-5
5'  CTGGTCAATACCTGCCATGG  3'

OLIGO-6
5'  GCTGAGAAAAATTGGTCG  3'

OLIGO-7
5'  GGCCGCGTTTACAGCTGCCATTTTTCTTAAGG  3'

OLIGO-8
5'  CGTACTCACTATGGCCAAAAAGCTATCC  3'

The cloned synthetic bovine gene for aFGF is converted to a human synthetic gene for aFGF by a series of directed point mutations. Oligonucleotide-directed mutagenesis of the cloned gene allows the alteration of the base sequence of bovine aFGF so that the resulting amino acid sequence contains the substituted amino acids shown in Table VIII and is human aFGF. A deletion is made in the bovine gene to remove the amino terminal phenylalanine for the production of the human 139 amino acid microheterogeneous form of aFGF. A point mutation is carried out to replace the second position asparagine with aspartic acid. Alternatively, the asparagine is deamidated to aspartic acid. The methods for carrying out these procedures are described below or are known in the art. The oligonucleotide-directed mutagenesis is carried out using standard procedures known to the art, Zoller and Smith, Methods in Enzymology, 100: 468–500 (1983) ; Norris et al., Nucleic Acids Research, 11: 5103–5112 1983); and Zoller and Smith, DNA, 3: 479–488 (1984). The point mutations of the bovine to human conversion are carried out by the standardized oligonucleotide-directed mutagenesis and are shown in the following Table. The location of the base mutagenesis can be seen in Table X.

TABLE X

| Base Location | Substituted Base Human aFGF | Substituted Base for Bovine aFGF | Corresponding Human Amino Acid |
|---|---|---|---|
| 22 | C | T | Pro |
| 69 | C | T | His |
| 112 | G | A | Arg |
| 148 | C | G | Ser |
| 159 | G | A | Val |
| 199 | A | T | Tyr |
| 324 | A | C | Asn |
| 354 | A | C | Ser |
| 358 | G | C | Cys |
| 364 | G | T | Arg |
| 365 | C | G | Arg |

TABLE X-continued

| Base Location | Substituted Base Human aFGF | Substituted Base for Bovine aFGF | Corresponding Human Amino Acid |
|---|---|---|---|
| 382 | A | T | Tyr |

To expedite the mutagenesis of the bovine aFGF gene it is transfered to a standard vector, M13mp19, a single-stranded DNA bacteriophage vector. The bovine pKK aFGF plasmid is cleaved with EcoRI and SalI and the resulting 440 bp fragment is gel purified. Vector M13mp19 RF DNA is cleaved with the same two endonucleases and the ends are subsequently dephosphorylated with bacterial alkaline phosphatase. The vector DNA and the aFGF gene fragment DNA are ligated and the mixture is used to transform E. coli DH5 cells. A phage clone containing the bovine aFGF gene is selected, M13mp19-baFGF.

The human oligomers shown in Table IX are phosphorylated and annealed individually to M13mp19-baFGF single-stranded phage DNA. Closed-circular double-stranded molecules are prepared with T4 DNA ligase and DNA polymerase I klenow fragment. The preparations were each used to transform competent JM105 cells and the resulting transformant plaques are selected by hybridization with the appropriate oligomer which is labeled using polynucleotide kinase. Single-stranded DNA is isolated from the phage clone containing the human oligmer 4 mutations and the above procedure is repeated using the human oligomer 5 to generate a clone containing both the oligomer 4 and 5 mutations.

In the following procedures the bovine-to-human sequence mutations in these M13-based clones were combined into one pBR322-based clone. RF DNAs were -prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Volumes of each fragment are collectively ligated to a gel-purified 3.7 kb EcoRI-SalI fragment from pBR322 with T4 DNA ligase and used to transform competent E. coli DH5 cells (BRL) as described by the supplier. A clone containing the mutations specified by all four mutant oligomers is selected by hybridization with radiolabeled probes prepared from each of the oligomers. The 140 bp KpnI-BamHI DNA fragment isolated from cleaved RF DNA of the human 3 mutant M13 clone is ligated to endonuclease cleavage products of this human 1-2-6-8 mutant DNA and transformed into DH5 competent cells to generate a clone with the human 1-2-3-6-8 mutations. BamHI-PstI digestion fragments of this latter clone are ligated to the BamHI-PstI digestion fragments of RF DNA from the human 4-5 M13-based clone and the ligation mixture is used to transform DH5 competent cells. A clone containing the human 1-2-3-4-5-6-8 mutations is selected by oligomer hybridization and the aFGF gene EcoRI-SalI DNA fragment of this recombinant plasmid is ligated to phosphatase-treated EcoRI-SalI-cleaved RF DNA of M13mp18 (BRL). Competent DH5 cells are transformed with this ligated DNA and the transformed cells are plated on JM105 host cells to generate an M13 clone. The single-stranded phage DNA of this clone was annealed with the human 7 oligomer and an M13 clone containing all the desired mutations was obtained following the procedure described above. The human aFGF clone is designated M13mp18-haFGF.

Pure aFGF in the absence of heparin becomes less active presumably due to the generation of incorrectly stabilized intramolecular disulfide bonds and aggregates formed by intermolecular disulfide bonds. The covalent disulfide bonds are formed between two cysteine residues either in two separate polypeptide chains, interchain disulfide bond, or in different positions within a single chain, intrachain disulfide bond. In the case of enzymatic oxidative iodination, the active molecules can be recovered by reduction with 20 mM dithiothreitol in the presence of 3M guanidinium chloride at a pH of about 9.1. The present invention utilizes site directed mutagenesis for the specific substitution or deletion of amino acids capable of forming extraneous intramolecular or intermolecular covalent bonds and oxidation susceptable amino acids. Substitution as used herein refers to a deliberate change in the DNA base sequence of aFGF such that a desired amino acid is substituted for an undesired amino acid. The undesired amino acid may be one which forms unwanted covalent bonds, especially disulfide bonds, or one which is air-oxidizable either of which may decrease the biological activity of the molecule. A deletion as used herein refers to a deliberate change in the DNA base sequence of aFGF resulting in the elimination of the unwanted amino acid. The primary amino acid associated with intramolecular and intermolecular covalent bond formation is cysteine while the amino acids which are oxidization prone include cysteine, methionine and tryptophan. The cysteine residue or residues may be replaced with any amino acid which will not form disulfide bonds. The preferred amino acid for the substitution of cysteine is serine. The oxidation prone amino acids are replaced with any amino acid which is oxidation resistant, this includes, but is not restricted to, alanine, valine, leucine and isoleucine.

The invention is contemplated to include site-specific mutations of one or more of the cysteine residues and any non terminal methionine residue which could render native or recombinant aFGF less active or inactive due to the formation of incorrect intramolecular or intermolecular bonds or oxidative changes. The recombinant and native human and bovine protein contains two cysteine residues in common located at positions 16 and 83 and a methionine residue in common located at position 67 as defined by the native 140 amino acid form of both bovine and human aFGF. Bovine and human aFGFs each contain a third cysteine residue at positions 47 and 117, respectively. The common cysteine residues are the most likely to form a disulfide bond since the location of cysteine residues in disulfide bonds is highly conserved in homologous proteins. Thus the third cysteine residues that are in different locations in bovine and human aFGFs are very likely not found in disulfide linkages in the fully active proteins. It will be understood that the novel mutant aFGFs of the present invention will not only include the forms substituted at the non-common cysteine residues but also those that have all cysteines substituted or deleted, those in which any one or two of the cysteines have been substituted or deleted and those in which methionine has been substituted or deleted. The substitution or deletion of any one, especially the unique cysteine, all cysteine-s, two of the three cysteines or methionine in the human or bovine aFGF by site-directed mutagenesis may after the formation of unwanted intramolecular and intermolecular disulfide bonds and oxidized forms.

Site-specific mutagenesis is carried out on preferably bovine or human r-aFGF produced from genomic DNA, cDNA or by construction of genes for one or more of the microheterogeneous forms of the protein based on the microheterogeneous forms of aFGF from mammalian species including man. Genomic DNA is extracted from mammalian brain or pituitary cells and prepared for cloning by either random fragmentation of high molecular weight DNA following the technique of Maniatis et al., Cell 15: 687-701 (1978) or by cleavage with a restriction enzyme by the method of Smithies et al., Science 202: 1284-1289 (1978). The genomic DNA is then incorporated into an appropriate cloning vector, generally E. coli lambda phage, see Maniatis et al., Molecular Cloning, A Laboratory Manual, Cold Spring Harbor Laboratory, Cold Spring Harbor, N.Y. (1982).

To obtain cDNA for aFGF, poly (A)-containing RNA is extracted from cells that express aFGF by the method of Aviv and Leder, Proc. Natl. Acad. Sci. 69: 1408-1412 (1972). The cDNA is prepared using reverse transcriptase and DNA polymerase using standard techniques, as described in Maniatis et al., Molecular Cloning, a Laboratory Manual, Cold Spring Harbor Laboratory, Cold Spring Harbor, N.Y. (1982). The cDNA is tailed and cloned into an appropriate vector, usually pBR322, by a technique similar to that of Wensink, et al., Cell 3: 315-325 (1974).

The clonal genomic DNA or cDNA libraries are screened to identify the clones containing aFGF sequences by hybridization with an oligonucleotide probe. The sequence of the oligonucleotide hybridization probe is based on the determined amino acid sequence of aFGF. Maniatis et al., supra, Anderson and Kingston, Proc. Natl. Acad. Sci. USA 80: 6838-6842 (1983) and Suggs et al., Proc. Natl. Acad. Sci. USA 78: 6613-6617 (1981) describe various, procedures for screening genomic and cDNA clones. The preferred procedure is to specifically point mutate the synthesized bovine and human genes as described above.

Site-specific mutagenesis is carried out on a human or bovine aFGF single-stranded bacteriophage recombinant clone, such as M13mp18-haFGF or M13mp19-baFGF following the procedures of Zoller, and Smith, Methods in Enzym. 100: 468-500 (1983), Norris et al., Nucleic Acids Res. 11: 5103-5112 (1983), and Zoller and Smith, DNA 3: 479-488 (1984). Three oligonucleotides for each species are designed to specify serine codons in place of each of the cysteine codons of the human aFGF gene at positions 16, 83 and 117 and at positions 16, 47 and 83 for the bovine gene. An oligonucleotide is designed to specify a leucine codon in place of the methionine codon of the human or bovine aFGF at position 67. The human oligomers synthesized are shown in the following table with the mutated bases underlined.

TABLE XI

| | | |
|---|---|---|
| Cysteine 1 (16) | 5' CCGTTAGAGGAGTAAAGAAGC | 3' |
| Cysteine 2 (83) | 5' GGAAAAGGGACTCCTCG | 3' |
| Cysteine 3 (117) | 5' CCGCGTTTAGAGCTGCC | 3' |
| Methionine (67) | 5' CCATCAGTGTCCAGGGCAAGG | 3' |

Similar oligomers are identified for the appropriate regions of the bovine aFGF gene and the specific mutations carried out as described below.

The human oligomers are -phosphorylated and annealed individually to M13mp18-haFGF or M13mp19-baFGF single-stranded DNA. A second strand of DNA is synthesized using the annealed oligomer as primer. Each cysteine mutated gene is used to transform an appropriate host such as competent E. coli DH5 cells. The transformed cells are plated on a lawn of an acceptable host for the M13 virus such as E. coli JM105 cells. The transformed plaques are selected by hybridization with the appropriately labeled oligomer. Conditions of hybridization are optimized for each probe to prevent retention of hybrids containing single base changes. Single-stranded DNA is isolated from phage clones containing each of the cysteine-to-serine mutations for DNA sequence analysis using the method of Sanger et al., Proc. Natl. Acad. Sci. USA 74: 5463–5467 (1977). RF DNAs are prepared for each clone, cleaved with EcoRI and SalI and purified by agarose gel electrophoresis. The purified 440 bp inserts are individually ligated to the 2.7 kb EcoRI-SalI DNA fragment of the pKK2.7 tac promoter expression vector. The ligated DNAs are used to transform competent DH5 cells and clones containing DNA with the mutated cysteine codons are selected by hybridization to the appropriate oligomer. Each aFGF gene insert is sequenced by the method of Maxam and Gilbert, Methods in Enzymology 65: 499–560 (1980). The clones containing the single base change from the original human DNA are designated: pKK-haFGF (Ser 16), pKK-haFGF (Ser 83) and pKK-haFGF (Ser 117); while the bovine DNA; is designated pKK-baFGF (Ser 16), pKK-baFGF (Ser 47) and pKK-baFGF (Ser 83), for the location of the substitution in the protein.

Substitution of any two or all three of the cysteine residues is accomplished by multiple point mutations or by combining restriction fragments of either human or bovine recombinant wild-type and the (Ser 16), (Ser 47), (Ser 83) and (Ser 117) mutant synthetic genes, cloned in M13mp19 for bovine and M13mp18 for human, and subcloned in pKK2.7 as described above. It is to be understood that the multiple mutations can be carried out with either the bovine or human single mutation aFGF constructs as described above, however, the following illustration will include only human aFGF. The pKK-haFGF (Ser 16,32) and pKK-haFGF (Ser 16,32) recombinants are constructed by introducing the 0.23 Kb EcoRl-BamHl fragment of M13mp18 (Ser 16) into pKK2.7 followed by insertion of the 0.2 Kb BamHl-SalI fragments either from M13mp18 (Ser 83) or from M13mp18 (Ser 117). The pKK2.7 vector is modified to remove the BamHl site upstream of the tac promoter while leaving the BamHl site in the multicloning sequence. Following digestion with the corresponding restriction enzymes, subsequent ligation and transformation of an appropriate host, clones are selected and screened for those containing plasmids with the expected molecular weight for the recombinants, about 3.1 Kb. An appropriate bacterial host may include, but is not limited to, E. coli DH5, JM105 or AB1899.

The mutant haFGF (Ser 16,83,117) is constructed by replacing the 0.13 Kb SphI-SalI fragment of pKK-haFGF (Ser 16,83), by the corresponding fragment of pKK-haFGF (Ser 117) that encodes for Ser instead of Cys in the 117 position. The 3 Kb SphI-SalI fragment of pKK-haFGF (Ser 16,83) is purified by preparative agarose gel electrophoresis, electroelution and ligated to the 0.13 Kb SphI-SalI fragment of pKK-haFGF (Ser 117) purified from a 5% polyacrylamide el in the same way. The purified fragments are ligated and recombinants selected as described above.

The pKK-haFGF (Ser 83,117) mutant is constructed by replacing the 0.3 Kb PstI fragment of pKK-haFGF, the non-mutated form, with the fragment pKK-haFGF (Ser 16,83,117) that includes the codons for Ser instead of Cys at positions 83 and 117 using the above techniques. Transformants are analyzed by PstI-SalI digestion to determine the orientation of the ligated fragments. All genes are sequenced by the dideoxy method of Sanger et al., Proc. Natl. Acad. Sci. USA 74:5463–5467 (1977).

Expression of a mutated aFGF gene is accomplished by a number of different promoter-expression systems in a number of different host cells. It is desired and intended that there be included within the scope of this invention, the use of other host cells and promoter-expression systems for the expression of the intact mutated aFGF gene. The host cells include bacteria, yeast, insect, and mammalian cells. The antigens may also be expressed in viruses. Although the genes can be expressed in numerous procaryotic cells and various eucaryotic cells the preferred host cell is Escherichia coli. The expression vectors which can be used for the expression of the mutated aFGF include, but are not limited to, pBR322, pPLa2311, pKC30, ptac12, λgt11, CheY, pAS1, pLC24, pSB226, SV40 and pKK223-3 with pKK223-3 being preferred. Escherichia coli expression vectors generally allow the translation of a methionine residue attached to the first amino acid of the desired protein. It will be understood that the present invention includes not only mutant r-aFGF with a terminal methionine but also mutant r-aFGF which has had the terminal methionine removed following translation in such cell types as yeast cells, mammalian cells or bacterial cells. The expression vector may have included in the DNA sequence one or more additional cistrons which will enhance the expression of the aFGF gene, Schoner et al., Proc. Natl. Acad. Sci USA 83: 8506–8510 (1986). The preferred construct uses the E. coli tac promoter, a hybrid between regions of the trp promoter and the lac promoter as described by deBoer et al., Proc. Nat. Acad. Sci. USA 80: 21–25 (1983). Plasmid pKK 223-3 (Pharmacia) which contains the tac promoter and rrnB rRNA transcription terminator was modified to remove the pBR322-derived SalI restriction enzyme site. The rrnB rRNA terminator has been shown to allow expression by strong promoters, Gentz et al., Proc. Natl. Acad. Sci. USA 78: 4936–4940 1981; Brosius Gene 27: 161–172 (1984).

The pKK223-3 plasmid DNA is cleaved with restriction enzymes to produce a 2.7 kb DNA fragment to generate clone pKK2.7. The synthetic aFGF gene is cleaved from its pBR322 vector and transferred to the pKK2.7 plasmid after restricting pKK2.7 with EcoRI and SalI. The resulting recombinant, shown in FIG. 1, is transformed into *E. coli* JM105 (Pharmacia) or DH5 (BRL) cells and expressed.

The preferred enhancing expression vector will contain a nucleotide sequence, the first cistron, upstream of the gene encoding the desired protein, the second cistron. The mutated aFGF will be the second cistron. The first cistron will generally contain a Shine-Dalgarno sequence upstream of the stop codon. An enhancing expression vector may contain, but is not limited to, the following nucleotide sequence:

```
         AATTATGTATCGATTAAATAAGGAGGAAT
             TACATAGCTAATTTATTCCTCCTTATTAA
(pKK.2.7)      (cistron 1,2 oligomers)            (aFGF)
``` which is an effective first cistron for enhancing the expression of wild-type or mutant aFGF. The first cistron is inserted into the appropriate pKK haFGF construct at the EcoRl site. The insertion results in the loss of the EcoRl cloning site. The recombinant is transformed into an appropriate host cell such as those described above and expressed. This construct results in about a 10-fold increase in wild type or mutant aFGF expression. The plasmids containing the enhancing expression vector are designated pKK2c-haFGF. The present invention is contemplated to include clones containing the enhancing expression vector such as; pKK2c-haFGF (Ser 16), pKK2c-haFGF (Ser 83), pKK2c-haFGF (Ser 117), pKK2c-haFGF (Ser 16,83), pKK2c haFGF (Ser 16,117), pKK2c-haFGF (Ser 83,117), pKK2c-haFGF (Ser 16,83,117).

The mutated expression clones are grown at about 37° C. in an appropriate growth medium, which consists of about 1% tryptone, about 0.5% yeast extract, about 0.5% NaCl, about 0.4% glucose and about 50 µg/ml ampicillin. When the optical density at 550 nm reaches about 0.5, isopropyl-β-D-thiogalactopyranoside (IPTG) may be added to give a final concentration of about 1 mM and growth is continued at about 37° C. for up to about 24 hours. The cells from 1 liter of culture medium are harvested by centrifugation and resuspended in a washing buffer containing about 100 mM phosphate and about 5 mg/ml EDTA. After the final resuspension about 0.1 mg/ml of lysozyme is added and the suspension is incubated with gentle shaking at about 30° C. for about 15 minutes. The cells are collected by centrifugation and resuspended in a disruption buffer containing about 100 mM sodium phosphate at about pH 6.0, about 3 mM EDTA, about 0.03 mM N-p-toluenesulfonyl-L-phenyl-alanine chloromethyl ketone (TPCK), about 0.05 mM pepstatin A, about 0.05 mM phenylmethylsulfonyl fluoride (PMSF), about 0.05 mM leupeptin and about 15 µg/ml bovine pancreatic trypsin inhibitor (BPTI). The cells are either immediately disrupted or frozen and stored at −70° C. and disrupted immediately after thawing by about two passages through a French pressure cell at about 20,000 psi at about 4° C. The supernatant fluid is collected following centrifugation and lyophilyzed.

The mutated aFGFs are purified to homogeneity by a three step chromatography process employing a cation exchanger matrix followed by a Heparin-Sepharose affinity matrix followed by reverse phase high performance liquid chromatography (HPLC). The lyophilyzed supernatant fluids are resuspended in phosphate buffer, about 100 mM, about pH 6.0 and added to a cation exchanger, preferably CM-Sephadex which has been equilibrated with the same buffer. The CM-Sephadex is added at a ratio of about 6.5 ml of settled resin per gram of protein. The resin is collected in a scintered lass funnel and washed three times with phosphate buffered saline, about 100 mM phosphate and about 150 mM NaCl at a pH of about 6. The resin is resuspended in the same buffer, packed in a column, washed and eluted with about 600 mM NaCl buffer. Heparin Sepharose is equilibrated with about 10 mM phosphate buffer, pH about 7.2 added to the eluate at a ratio of about 1 ml of settled resin per 1 mg of protein, gently shaken for about 1 hour at about 4° and the resin-protein complex collected in a funnel. The resin is resuspended in the same buffer and packed in a column at 1-2 column volume per hour. The column was washed with a buffer containing about 10 mM phosphate, pH about 7.2 and about 0.8M NaCl and eluted with 1.5M NaCl in the same buffer. Each protein was collected and further purified by reverse phase HPLC. Fractions are loaded on an HPLC reversed phase column, about $C_3$, equilibrated with about 10 mM trifluoroacetic acid (TFA) and eluted with a gradient of from about 0 to about 100% 4 mM TFA, about 0-67% $CH_3CN$ in about 30 minutes.

Mitogenic activity of the purified mutated recombinant aFGFs is determined by incorporation of $^3H$-thymidine into DNA by cell line fibroblasts, preferably BALB/c 3T3 A31 (American Type Culture Collection). Mutant proteins from plasmids pKK-haFGF (Ser 16) and pKK-haFGF (Ser 83) stimulated fibroblasts at a level equal to or lower than the non-mutated human aFGF. Mutant protein pKK-haFGF (Ser 117) showed a stimulatory activity that is higher than the non mutated forms in the absence of heparin.

A well controlled and very reproducible mitogenic assay is required to compare the relative I5 specific mitogenic activities of wild-type haFGF and the Cys to Ser mutants. Confluent cultures of Balb/c 3T3 cells in serum free culture fluid were stimulated with consecutive two-fold dilutions over at least 3 log orders of aFGF concentration spanning the complete rise of the response from background through peak DNA synthesis. One stimulatory unit is calculated as the amount of aFGF per ml that generated a half maximal response. The specific mitogenic activity is the number of stimulatory units per any of pure aFGF. The assay is further standardized by diluting stock solutions to about 50 µg aFGF/ml of $TFA/CH_3CN$, or less. The dilution eliminates any concentration effect so that different samples can be compared.

Conversion of the Cys 117, any two Cys or all three Cys residues to Ser results in a 7 to 20 fold increase of the specific activity of the protein in the absence of heparin. Even in the presence of heparin, all 4 multiple mutants are are more active than wild type human r-aFGF with haFGF (Ser 83,117) being about 2.7-fold more active. Although heparin stimulates the activity of wild-type aFGF 20-fold, it potentiates the activity of the mutants by only about 3- to about 5-fold.

Conversion of either all, or of any two, of the three Cys residues of human aFGF to Ser results in a 7 to 20 fold increase of the specific activity of the protein in the absence of heparin. Even in the presence of heparin, all four multiple mutants are more active than non-mutated haFGF, with haFGF Ser (83,117) being nearly 3-fold more active.

Mutated recombinant aFGF is useful in promoting the repair or healing of, but not limited to, soft tissue wounds resulting from burns, cuts or lacerations, and cutaneous ulcerations along with musculo-skeletal wounds such as bone fractures, ligament and tendon tears, and inflammation of bursas and tendons Tissue repair as used herein is defined as the regeneration of tissue following the stimulation of mesodermal, ectodermal or neuroectodermal derived cells by aFGF. Mutated r-aFGF is also useful in promoting the healing and regeneration of cartilage and cartilageneous tissue. Administration of mutated aFGF for soft tissue repair, including corneal tissue, will generally be by topical, subcutaneous, intravenous or intraocular application. Soft tissue includes all tissue except that associated with the musculo-skeletal system as described above. The novel peptides may be administered with or without heparin, preferably without heparin, about 0.1 to about 100 $\mu$g/cm$^2$/day of this invention, protein, to the wound area either topically or subcutaneously about 1 to about 100 $\mu$g/cm$^3$/day. The most preferred application range for topical administration is about 1 to about 10 $\mu$g/cm$^2$/day.

Heparin is a sulfated glycosaminoglycan consisting of equal parts of the sugars D-glucosamine and D-glucuronic acid which are sulfated to varying degrees. It is commercially available in an unmodified form as well as in a solution form for direct therapeutic utilization. When heparin is administered with aFGF in topical or subcutaneous applications the preferred concentration is from about 3 times to about 30 times the amount (mass) of aFGF administered per day.

For musculo-skeletal and cartilage repair or healing, the mutated r-aFGF is preferably administered at the site of the injury either during surgery or by injection. Surgical implantation of slow-release forms of the mutated aFGF will allow for a continued release of the growth factor for a prolonged period of time. Methods of formulation of mutated aFGF for slow release are known in the art. Dosage levels for musculo-skeletal healing will be about 10 to about 100 $\mu$g/cm$^3$/day.

Mutant r-aFGF is furthermore useful in promoting the facilitation of in vivo vascular tissue repair, such as blood vessel growth (angiogenesis), and vessel repair (such as the replacement of damaged endothelial cells) and in stimulating endothelial cell growth on appropriate substrates for the production of blood vessels for implantation. In vivo angiogenesis activity of the novel mutant r-aFGF peptides is accomplished by the internal administration, such as subcutaneously, of about 1 to 1000 $\mu$g/cm$^3$/day with the more preferred amount of about 10 to about 100 $\mu$g/cm$^2$/day. The preferred application range for surface repair is about 100 ng to about 100 $\mu$g/cm$^2$/day with the most preferred application range being about 1 to about 10 $\mu$g/cm $^2$/day. Large vessel repair is accomplished by a single dose of about 0.1 to about 100 ng/cm$^3$ or by continuous infusion of about 1 to about 1000 pg/cm$^3$/day. In vitro growth of Endothelial cells on appropriate substrates for the production of blood vessels is accomplished by the administration of about 1 to about 10 ng/ml/day.

Mutant r-aFGF is also useful in the in vivo induction of plasminogen activator by vascular endothelial cells for the treatment of thrombotic attacks. Thrombotic attacks result form the formation of thrombi within blood vessels which may result in thrombotic strokes, deep vein thrombosis, myocardial infarction and other medical conditions which give rise to necrosis of tissues and often times death of the patient. Digestion of preformed clots and the prevention of further clot formation can be mediated by mutant r-aFGF thereby enhancing the treatment of thrombotic attacks. Pretreatment with mutant r-aFGF may also be used to prevent the formation of clots in animals, including man, which are at high risk for clot formation. The desirable dosage range of mutant r-aFGF for the treatment of thrombotic attack is about 10 $\mu$g–10 mg/kg/day.

Mutated and wild-type r-aGFG is also useful in promoting central and peripheral nerve tissue repair including the maintenance and stimulation of hippocampal neurons and neurons that are damaged or destroyed in Alzheimer's disease and motor and sensory neurons whose destruction causes paralysis. Damaged nervous tissue may be stimulated by mutated or wild-type aFGF to produce additional neurons by mitosis of neuroblasts to re-populate the damaged nerves in the area and to promote neurite outgrowth from neurons. The peptides may be administered as described for wound healing of either soft tissue or musculo-skeletal tissue.

For topical application, various pharmaceutical formulations are useful for the administration of the active compound of this invention. Such formulations include, but are not limited to the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxyalkyl celluloses and alkylhydroxyalkyl celluloses, for example methylcellulose, hydroxyethyl cellulose, carboxymethyl cellulose, hydroxypropyl methylcellulose, and hydroxypropyl cellulose; poloxamers such as Pluronic ® Polyols exemplified by Pluronic F-127; tetronics such as tetronic 1508; and alginates such as sodium aliginate. The pharmaceutical formulations will include one or more of the mutated aFGF compounds in amounts of about 0.1 to about 100 $\mu$g/ml.

For non-topical application the mutant r-aFGF is administered in combination with pharmaceutically acceptable carriers or diluents such as, phosphate buffer, saline, phosphate buffered saline, Ringer's solution, and the like, in a pharmaceutical composition, according to standard pharmaceutical practice.

The ability of mutated aFGF to stimulate division in various cell types including fibroblasts, vascular and corneal endothelial cells and the like makes these peptides useful as pharmaceutical agents. These compounds can be used to treat wounds of mammals including humans by the administration of the novel mutated r-aFGF to patients in need of such treatment.

The following examples illustrate the present invention without, however, limiting the same thereto.

EXAMPLE 1

Oligonucleotide Synthesis

Oligonucleotides were synthesized according to the technique described by Matteucci and Caruthers, J. Am. Chem. Soc. 103: 3185-3191 (1981); Beaucage and Caruthers, Tetrahedron Letters 22: 1859-1862 (1981). The base sequences of the synthesized oligonucleotides are shown in Tables VII, IX and XI.

EXAMPLE 2

Assembly of the aFGF Gene

The bovine oligonucleotides from Example 1 were assembled as two separate units, the N-terminal half (231 bp) and the C-terminal half (209 bp). The two halves were then combined for the intact synthetic gene, see Table VI. Initially the oligonucleotides were kinased in the following reaction mixture: 70 mM Tris pH 7.6, 5 mM DTT, 10 mM MgCl$_2$, 33 μM ATP, 0.3 units T4 polynucleotide kinase per μl, and 2.5 pmole oligonucleotide per μl. The mixture was incubated 1.5 hours at 37° C. and then an additional hour after supplementing the mixture with 0.2 units/μl kinase and ATP to give a concentration of 100 mM. For radioactive labelling, the initial mixture contained 37 nCi/μl of [γ-$^{32}$P]-ATP.

The annealing and ligations were done in two each reaction, 100 pmole of separate reactions. In each of the eight oligonucleotides were added. In one reaction the oligonucleotides which make up one strand of the C-terminal or N-terminal half gene were kinased with the exception of the most 5' oligonucleotide. In the second reaction the oligonucleotides which make up the opposite strand were kinased, again with the exception of the most 5' oligonucleotide. Thus, in each reaction 3 oligonucleotides were kinased and 5 were not. When kinased oligonucleotides were used, 1 pmole of the $^{32}$P-labelled oligonucleotide was also added for later identification of the products. Each reaction contained 200 μl with 70 mM Tris pH 7.6, 5 mM DTT, 10 mM MgCl$_2$, and 30 μM ATP. The oligonucleotides were annealed by heating to 90° C. for 4 minutes, then immediately transferring the reaction to 60° C. and allowing it to cool slowly to 30° C. Ligation was done in 400 μl containing 60 mM Tris pH 7.6, 10 mM DTT, 10 mM MgCl$_2$, 1 mM ATP, and 0.03 units T4 DNA ligase per μl by incubating at 20° C. for 1.5 hours.

Polyacrylamide gel electrophoresis was used to purify the ligated oligonucleotides. The ligated oligonucleotides were precipitated with ethanol, redissolved in 20 μl of 80% formamide, 50 mM TRIS-borate pH 8.3, 1 mM EDTA, 0.1% (w/v) xylene cyanol, and 0.1% (w/v) bromophenol blue. Each sample was heated at 90° C. for 3 minutes and electrophoresed in a 10% urea-polyacrylamide gel at 75 watts for 5 hours. The oligonucleotide bands were visualized by exposing the gel to X-ray film.

The 231 base bands of each reaction for the N-terminus were cut out of the gel, combined, and eluted at 4° C. in 1 ml of 0.5M ammonium acetate, 1 mM EDTA pH 8. The eluted DNA was precipitated with ethanol and redissolved in 30 μl of 70 mM Tris pH 7.6, 5 mM DTT, and 10 mM MgCl$_2$. The 209 base bands of the C terminus were eluted in the same manner.

The gel purified oligonucleotides were annealed prior to transformation by heating to 90° C. for 4 minutes and slow cooling to 20° C. Assuming a 5% recovery from the initial starting oligonucleotides, 300 fmole and 100 fmole of recovered annealed 231 bp oligonucleotides were each ligated to 100 fmole of agarose gel purified 3.9 kb EcoRI-BamHI pBR322 fragment DNA in 20 μl of 25 mM Tris pH 7.8, 1 mM DTT, 10 mM MgCl$_2$, 0.4 mM ATP, with 1 unit T4 DNA ligase for 1 hour at 20° C. The annealed 209 bp oligonucleotides were ligated to agarose purified 3.9 kb BamHI-SalI pBR322 fragment DNA under the same conditions as the 231 base pair fragments. The ligation reactions were diluted 1:5 in H$_2$O and 1 μl of dilution was used to transform 20 μl of competent *E. coli* RR1 cells (BRL) as described by the supplier. The transformants were selected for growth in ampicillin and screened for the presence of the 231 bp EcoRI-BamHI or the 209 bp BamHI-SalI insert by restriction analysis of mini-lysate plasmid preparations.

The DNA sequence of clones containing the appropriate sized inserts was determined using the chemical DNA sequence techniques of Maxam and Gilbert, Proc. Natl. Acad. Sci. USA 74: 560-564 (1977). Since none of the 231 bp clones had the correct sequence, a clone containing the correct sequence was prepared as follows. One clone with the correct sequence between the KpnI and BamHI sites was cleaved with KpnI and with SalI, which cleaves in the pBR322 vector. The 400 bp band was gel purified and ligated to the 3.8 kb KpnI-SalI band of a second clone containing the correct sequence from the EcoRI site to the KpnI site of the aFGF gene insert. After transformation, a resulting clone was sequenced to ensure the desired sequence had been obtained.

Since a clone containing the correct 209 bp sequence was obtained, no further manipulation of these clones was required. The final full-length aFGF synthetic gene was cloned by cleaving the N-terminal half clone with BamHI and SalI, treating with alkaline phosphatase, and ligating this to the gel purified 209 bp BamHI-SalI insert of the C-terminal half clone. This ligated material was used to transform competent RR1 cells as before.

EXAMPLE 3

Mutagenesis of the Bovine aFGF Gene to the Human aFGF Gene

To facilitate the mutagenesis of the bovine aFGF gene, the synthetic gene from Example 2 was transferred to M13mp19, a single-stranded DNA bacteriophage vector. Standard mutagenesis procedures were used as reported by Zoller and Smith, Methods in Enzymology, 100: 468-500 (1983); Norris et al., Nucleic Acids Research, 11: 5103-5112 (1983); and Zoller and Smith, DNA, 3: 479-488 (1984). The bovine pKK-aFGF plasmid was cleaved with EcoRI and SalI and the resulting 440 bp fragment was agarose gel purified as in Example 2. Vector M13mp19 RF DNA (BRL) was cleaved with the same two endonucleases and the ends were subsequently dephosphorylated in 100 μl of 10 mM Tris pH 8.0 buffer with 100 units of bacterial alkaline phosphatase. A ligation was performed using 50 ng of the treated vector DNA and 12 ng of the aFGF gene fragment DNA in 10 μl of 25 mM Tris pH 7.8, 10 mM MgCl$_2$, 1 mM DTT, 0.4 mM ATP, with 2 units of T4 DNA ligase for 16 hours at 4° C. The reaction mixture was diluted 1:5 in H$_2$O and 1 μl of dilution was used to transform 20 μl of competent *E. coli* DH5 cells (BRL) as described by the supplier. The cells were plated with *E. coli* JM105 (Pharmacia) host cells in 0.03% X-gal and 0.3 mM IPTG; after incubation at 37° C. colorless plaques were isolated. One phage clone containing the bovine aFGF gene was selected, M13mp19-baFGF.

Eight oligonucleotides were designed to specify the human sequence and synthesized, see Table IX. Oligomer 8 contains an additional mutation in which thymine at site 386 in the bovine gene is replaced by cytosine in the human gene. This mutation allows the incorporation of a restriction site without altering the human aFGF amino acid sequence.

The human oligomers 1, 2, 3, 4, 6, and 8 were phosphorylated and 15 pmoles of each were annealed individually to 0.5 pmole of M13mp19-baFGF single-stranded phage DNA in 10 μl of 20 mM Tris pH 7.5, 10 mM MgCl$_2$, 50 mM NaCl, 1 mM DTT for 10 minutes at 65° C. followed by 10 minutes at 23° C. Closed-circular double-stranded molecules were then prepared in 20 μl of 20 mM Tris pH 7.5, 10 mM MgCl$_2$, 25 mM NaCl, 5.5 mM DTT, 0.5 mM ATP, 0.25 mM dATP, 0.25 mMd CTP, 0.25 mM dGTP, 0.25 mM dTTP, using 1 unit of T4 DNA ligase and 2 units of DNA polymerase I klenow fragment by incubation at 15° C. for 17 hours. The preparations were each used to transform competent JM105 cells and the resulting transformant plagues were selected by hybridization with the appropriate oligomer which had been radio-labeled using $^{32}$P-ATP and polynucleotide kinase. The conditions of hybridization were optimized for each probe to prevent formation of hybrids containing single base changes. Single-stranded DNA was isolated from the phage clone containing the human oligomer 4 mutations and the above procedure was repeated using the human oligomer 5 to generate a clone containing both the oligomer 4 and 5 mutations.

In the following procedures the bovine-to-human sequence mutations in these M13-based clones were combined into one pBR322-based clone. RF DNAs were prepared from clones containing the base changes specified by human oligomers 1, 2, 6, and 8. The DNA of the human 1 mutant clone was cleaved with EcoRI, the ends were dephosphorylated with bacterial alkaline phosphatase, and the DNA was cleaved with HindIII. The human 2 mutant DNA was cleaved with HindIII, treated with phosphatase, and then cleaved with BamHI. The human 6 mutant DNA was cleaved with BamHI, phosphatase treated, and subsequently cleaved with ApaI. Likewise, the human 8 mutant DNA was cleaved with ApaI, the ends were dephosphorylated, and the DNA was cleaved with SalI. These four DNA preparations were electrophoresed through 2% agarose and the fragments of 45 bp, 190 bp, 135 bp, and 70 bp from the mutant DNAs containing human 1, 2, 6, and 8 mutations, respectively, were eluted from the gel. Approximately 60 fmoles of each fragment were collectively ligated to about 60 fmoles of a gel-purified 3.7 kb EcoRI-SalI fragment from pBR322 in 5 μl of 25 mM Tris pH 7.8, 10 mM MgCl$_2$, 1 mM DTT, 0.4 mM ATP, with 1.5 units of T4 DNA ligase for 16 hours at 12° C. The reaction mixture was diluted 1:5 in H$_2$O and 1 μl of dilution was used to transform 20 μl of competent E. coli DH5 cells (BRL) as described by the supplier. A clone containing the mutations specified by all four mutant oligomers was selected by hybridization with radiolabeled probes prepared from each of the oligomers. The 140 bp KpnI-BamHI DNA fragment isolated from cleaved RF DNA of the human 3 mutant M13 clone was ligated to endonuclease cleavage products of this human 1-2-6-8 mutant DNA and transformed into DH5 competent cells to generate a clone with the human 1-2-3-6-8 mutations. BamHI-PstI digestion fragments of this latter clone were ligated to the BamHI-PstI digestion fragments of RF DNA from the human 4-5M13-based clone and the ligation mixture was used to transform DH5 competent cells. A clone containing the human 1-2-3-4-5-6-8 mutations was selected by oligomer hybridization and the aFGF gene EcoRI-SalI DNA fragment of this recombinant plasmid was ligated to phosphatase-treated EcoRI-SalI-cleaved RF DNA of M13mp18 (BRL). Competent DH5 cells were transformed with this ligated DNA and the transformed cells were plated on JM105 host cells to generate an M13 clone. The single-stranded phage DNA of this clone was annealed with the human 7 oligomer and an M13 clone containing all the desired mutations was obtained following the procedure described above. RF DNA was prepared from this clone and cleaved with EcoRI and SalI. The resulting 440 bp band was gel purified and ligated to the 2.7 kb EcoRI-SalI DNA fragment of the pKK2.7 tac promoter expression vector. This DNA was used to transform competent DH5 cells thus generating the human pKK-aFGF expression clone used for production of the human form of aFGF.

EXAMPLE 4

Mutagenesis of the Cysteine Codons of the aFGF Gene

A human aFGF single-stranded bacteriophage recombinant clone, M13mp18-haFGF, from Example 3 was mutagenized using procedures reported by Zoller and Smith, *Methods in Enzymology*, 100: 468–500 (1983); Norris et al., *Nucleic Acids Research*, 11: 5103–5112 (1983); and Zoller and Smith, *DNA*, 3: 479–488 (1984). Three oligonucleotides were designed to specify serine codons in place of each of the cysteine codons of the human aFGF gene at positions 16, 83, and 117. The oligomers synthesized are shown in Table XI with the mutated bases underlined.

The oligomers were phosphorylated and 15 pmoles of each were annealed individually to 330 ng of M13mp18 haFGF single-stranded DNA in 10 ul of 20 mM Tris pH 7.5, 10 mM MgCl$_2$, 50 mM NaCl, and 1 mM DTT for 10 minutes at 65° C. followed by 10 minutes at 23° C. A second strand of DNA was synthesized using the annealed oligomer as primer in 20 ul of 20 mM Tris pH 7.5, 10 mM MgCl$_2$, 25 mM NaCl, 5.5 mM DTT, 0.5 mM ATP, 0.25 mM dATP, 0.25 dCTP, 0.25 mM dGTP, 0.25 mM dTTP, using 3 units of T4 DNA ligase and 0.4 units of DNA polymerase I klenow fragment by incubation at 12° C. for 17 hours. The three preparations were each diluted 1:5 in H$_2$O and 1 ul of dilution was used to transform 20 ul aliquots of competent E. coli DH5 cells (Bethesda Research Labs) as described by the supplier. The transformed cells where plated with a lawn of E. coli JM105 cells which act as host cells for the M13 virus. The resulting transformant plagues were selected by hybridization with the appropriate oligomer which had been radio-labeled using $^{32}$P-ATP and polynucleotide kinase. The conditions of hybridization were optimized for each probe to prevent retention of hybrids containing single base changes.

Single-stranded DNA was isolated from phage clones containing each of the cysteine-to-serine mutations for DNA sequence analysis using the dideoxynucleotide chain termination method of Sanger et al., Proc. Natl. Acad. Sci. USA 74:5463–5467 (1977). RF DNAs were then prepared from three clones, each containing one of the specified mutations, and after cleavage with EcoRI and SalI the released FGF gene inserts were isolated by agarose gel electrophoresis. The purified 440 bp inserts were each ligated to the 2.7 kb EcoRI-SalI DNA fragment of the pKK2.7 tac promoter expression vector in 10 ul of 25 mM Tris pH 7.8, 10 mM MgCl$_2$, 1 mM DTT 0.4 mM ATP, with 3 units of T4 DNA ligase for 2 hours at 14° C. The ligated DNAs were used to transform competent DH5 cells and clones containing DNA with the mutated Cys codons were selected by hybridization to the appropriate oligomer. The FGF gene insert in the plasmid DNA of these clones was sequenced completely by the chemical method of Maxam and Gilbert, Methods in Enzymology 65:499–560 (1980). One clone contained only the single base change from the original human aFGF expression clone generating a serine codon in place of a cysteine codon at position 83 and is designated as pKK-haFGF(Ser 83).

The clones containing each of the other two cysteine-to-serine mutations also contained additional non-specified changes. In order to generate the desired single base mutants the following ligations and transformations were performed. The 410 bp HindIII-derived DNA fragment of the clone with the serine codon at position 16 was isolated and ligated to the 2.7 kb HindIII-derived fragment of the original pKK-haFGF expression clone. The 230bp NcoI-SalI-derived DNA fragment of the clone containing the serine codon at position 117 was isolated and ligated to the 2.9 kb NcoI-SalI derived fragment of pKK-haFGF. Each of these ligated samples was used to transform competent DH5 cells; hybridization and sequencing techniques were used to identify the other two desired single base mutants designated pKK-haFGF(Ser 16) and pKK-haFGF(Ser 117). These three clones were used for production of the Ser 16, Ser 83, and Ser 117 forms of the human aFGF.

Site-directed mutants of human aFGF with two or three cysteine (Cys) residues converted to serine (Ser) residues were constructed by combining restriction fragments of the non mutated wild-type and the Ser (16), Ser (83) and Ser (117) mutant synthetic genes, have been cloned in pKK2.7 and subcloned in M13mp18, as described above. The pKK-haFGF (Ser 16,83) and pKK-haFGF (Ser 16,117) recombinants were constructed first by introducing the 0.23 Kb EcoRI-BamHI fragment of M13mp18 (Ser 16), that includes the codon for Ser 16, into pKK2.7 followed by insertion of the 0.2 Kb BamHI-SalI fragments either from M13mp18 (Ser 83) or from M13mp18 (Ser 117). Since the pKK2.7 vector contains two BamHI sites, one in the multicloning sequence and the second one upstream of the tac promoter, a modified pKK2.7 vector, in which the second upstream BamHI site was eliminated, was used in these constructions. After digestion with the corresponding restriction enzymes, subsequent ligation and transformation of AB1899 competent cells (*E. coli* Genetic Stock Center), ampicillin resistant clones were selected and screened for those containing plasmids with the expected molecular weight for the recombinants (3.1 Kb).

The mutant haFGF (Ser 16,83,117) was constructed by replacing the 0.13 Kb SphI-SalI fragment of pKK-haFGF (Ser 16,83), by the corresponding fragment of pKK (Ser 117) that encodes for Ser instead of Cys in position 117. The 3 Kb SphI-SalI fragment of pKK (Ser 16,18) was purified by preparative agarose gel electrophoresis, electroelution and ligated to the 0.13 Kb SphI-SalI fragment of pKK (Ser 117) purified from a 5% polyacrylamide gel in the same way. The purified fragments were ligated and recombinants were selected for ampicillin resistance after transformation of AB1899 cells.

For construction of pKK haFGF (Ser 83,117), the 0.3 Kb PstI fragment of pKK haFGF was replaced with the same fragment of pKK-haFGF (Ser 16,83,117) that includes the codons for Ser instead of Cys at positions 83 and 117 using basically the same strategy. AB1899 transformants selected for ampicillin resistance were analyzed by PstI-SalI digestion to determine the orientation of the ligated fragments. All mutant genes were sequenced by the dideoxy method using the Sequence kit of USB Corp.

EXAMPLE 5

Expression of the Synthetic Bovine aFGF Gene

The intact aFGF genes from Example 4 were incorporated into a modified pKK223-3 plasmid. The pKK223-3 plasmid (Pharmacia) contains the tac promoter which is a hybrid between regions of the trp promoter and the lac promoter, deBoer et al., Proc. Natl Acad. Sci. USA 80: 21–25 (1983). This plasmid also contains the rrnB rRNA transcription terminator, a strong terminator sequence found to allow expression from strong promoters, Gentz et al., Proc. Natl. Acad. Sci. USA 78: 4936–4940 (1981); Brosius, Gene 27: 161–172 (1984). The pKK223-3 plasmid was modified to remove the pBR322-derived SalI restriction enzyme site. This was accomplished by cleaving the pKK223-3 plasmid DNA with NdeI and NarI, blunt-ending the DNA fragment with Klenow DNA polymerase, and recircularizing the 2.7 kb DNA fragment to generate clone pKK2.7. The synthetic aFGF gene was then cleaved from its pBR322 vector and transferred to pKK2.7 after restricting this expression vector with EcoRI and SalI. This construction positions the initiating methionine of the synthetic gene 11 bases downstream of the Shine-Dalgarno ribosome binding site. The resulting recombinant vectors, as exemplified by FIG. 1, were transformed into *E. coli* JM105 cells and also into *E. coli* DH5 cells.

The expression clones were grown at 37° C. in LB broth (1% tryptone, 0.5% yeast extract, 0.5% NaCl) containing 0.4% glucose and 50 μg/ml ampicillin. When the optical density at 550 nm reached 0.5, IPTG was added to give 1 mM and growth was continued at 37° C. for 3 hours. The cells were harvested by centrifugation at 10,000×g for 20 minutes and the cells from 1 liter of culture were resuspended in glycerol/phosphate buffered saline 1:1 and quickly frozen in a dry ice/ethanol bath and stored overnight at −70° C.

EXAMPLE 6

Enhanced Expression Vector

Enhanced levels of expression for the mutated forms of aFGF of Example 4 were provided by modification of the expression vector of Example 3 to introduce an additional cistron upstream of the aFGF encoding sequence. Two oligonucleotides were synthesized with the sequences as shown at page 40. When annealed these oligomers supply 5' extensions of 4 bases which are complementary to the extensions provided by EcoRI cleavage, a 7 codon open reading frame following the ATG translation initiation codon and preceding a TAA stop codon, and an additional Shine-Dalgarno ribosome binding site located within the open reading frame upstream of the stop codon. Using 1 pmole of each oligomer, the oligomers were annealed together in 20 μl of DNA ligase buffer by heating to 70° C. for 10 minutes and slow cooling. The annealed mixture, 0.3 pmole, was ligated to 0.1 pmole of EcoRI-cleaved pKK haFGF plasmid DNA in a final volume of 25 μl containing 3 units of T4 DNA ligase (Pharmacia) for 2.5 hours at 14° C. The ligated DNA, 5 ng, was used to transform competent *E. coli* JM105 cells. The transformants were screened by restriction analysis, as the EcoRI site is lost by this insertion, and by immunoblot analysis. The expression vector of one clone, which demonstrated higher levels of FGF production, was sequenced by the chemical technique of Maxam and Gilbert, supra, to verify the correct insertion of the new cistron sequences. Subsequently, this high expression pKK2c-haFGF vector was transferred to *E. coli* DH5 by transformation procedures.

In order to express the haFGF (Ser 117) mutant gene, for example, in this high expression vector, the 0.23 kb NcoI-SalI fragment of pKK-haFGF (Ser 117) was ligated to the 2.5 kb NcoI-SalI fragment of pKK2c-haFGF and transformed into competent cells. The other mutated haFGFs were transferred to the two cistron high expression vector in a similar manner, replacing appropriate restriction fragments containing the wild-type sequences of pKK2c-haFGF with the analogous restriction fragments of the mutated haFGF.

EXAMPLE 7

Extraction and Purification of Mutated aFGF

The frozen cells from Example 5 were thawed and resuspended in a quantity sufficient to make 50 ml with 100 mM phosphate buffer, pH 7.2, 5 mg/ml EDTA and the cells were collected by centrifugation at $28,000 \times g$ for 5 minutes. The cells were washed a second time, collected by centrifugation and resuspended in 50 ml of the same buffer. The extinctions of the three mutant strain suspensions at 660 nm were strain pKK-haFGF(Ser 117), 103; strain pKK-haFGF(Ser 16), 108; strain pKK-haFGF(Ser 83) 59. Each sample received 0.1 mg/ml of lysozyme and was incubated for 15 minutes with gentle shaking at 30° C. The cells were collected by centrifugation and resuspended in 50 ml of breaking buffer consisting of 100 mM phosphate; pH 6.0; 3 mM, EDTA; 0.05 mM, TPCK, 0.05 mM, Pepstatin A, 0.05 mM, Leupeptin and 15 μg/ml BPTI. Each cell suspension was kept at 4° C. and broken by two passages through a previously cooled French pressure cell at 20,000 psi at 4° C. The disrupted cell suspensions were centrifuged for 15 minutes at 15,000 rpm in a SS-34 Sorvall rotor and for 60 minutes at 45,000 rpm in a 70 Ti rotor in a Beckman ultracentrifuge at 4° C. The supernatant fluid was collected, the extinctions at 280 nm for a 55 ml volume were determined: pKK-haFGF(Ser 117), 44; pKK-haFGF(Ser 16), 40 and pKK-haFGF(Ser 83), 23 and the samples were frozen at $-70°$ C.

The supernatant fluids were thawed by the addition of 200 ml of 100 mM phosphate buffer, pH 6.0, containing CM Sephadex at a ratio of 6.5 ml of settled resin per gram of protein (assuming absorbance through a 1 cm path of a 1 mg/ml protein solution is 1.0). The sample was collected in a scintered glass funnel and washed three times with 200 ml of 100 mM phosphate buffer containing 150 mM NaCl at a pH of 6.0. The resin cake was resuspended in 200 ml of the same buffer, packed in a column at $12 \text{ ml} \times \text{hr}^{-1}$ per cm$^2$ crossectional ArGA and washed at the same flow rate with 150 mM phosphate buffer containing 600 mM NaCl. The fractions containing the protein eluted with the 600 mM NaCl buffer were pooled, the pH adjusted to 7.2 and the conductivity adjusted with deionized water to 10 $\mu\text{S} \times \text{cm}^{-1}$. Heparin-Sepharose (freshly prepared) equilibrated with 10 mM phosphate pH 7.2 (conductivity 1.3 $\mu\text{S} \times \text{cm}^{-1}$ was then added at a ratio of 1 ml of settled resin per mg of protein (using the same assumed extinction coefficient as above), the suspension gently shaken for one hour at 4° C., and the resin collected in a funnel, resuspended in the same buffer and packed in a column at 1-2 column volume per hour. The packed column was washed with 10 mM phosphate, 0.8M NaCl pH 7.2 at the same flow rate until the extinction of the eluate at 280 nm decreased to a steady value, to within 0.01 optical absorbance units above the elution buffer and then the buffer changed to 10 mM phosphate, 1.5M NaCl pH 7.2. The fractions containing the protein eluted with the 1.5M buffer (monitored by the extinction at 280 nm) were pooled together and loaded in a C$_3$ reversed phase HPLC column equilibrated with 10 mM TFA and eluted with a gradient from 0-67% CH$_3$CN in 30 minutes.

The purification data of the mutant strains is shown below:

pKK-haFGF(Ser 16)

Fractions 25-31 eluted from the CM-Sephadex column with the 0.6M NaCl buffer in a total volume of 24 ml and a protein content of 3.5 mg were made 125 ml with deionized water (final conductivity: 7 mS/cm) and 4 ml of heparin-Sepharose added. The column was run at 6 ml/h. Fractions 55-57 eluted with 1.5M NaCl, were injected on the C$_3$ column. From this column a major peak was collected with a protein content of 80 μg.

pKK-haFGF(Ser 83)

Fractions 19-33 eluted from the CM-Sephadex column with the 0.6M NaCl buffer in a total volume of 40 ml and a protein content of 4.0 mg were made 150 ml with deionized water (final conductivity: 10 mS/cm) and 4 ml of heparin-Sepharose added. The column was run at 6 ml/h. Fractions 40-44, eluted with 1.5M NaCl, were injected in the C$_3$ column. From this column a major peak was collected with a protein content of 80 μg.

pKK-haFGF(Ser7 117)

Fractions 19-33 eluted from the CM-Sephadex column with the 0.6M NaCl buffer in a total volume of 57 ml and a protein content of 11.4 mg were made 250 ml with deionized water (final conductivity: 12 mS/cm) and 10 ml of heparin-Sepharose added The column was run at 11 ml/h. Fractions 59-62, eluted with 1.5M NaCl, were injected in the C$_3$ column. From this column a major peak was collected with a protein content of 614 μg.

The protein products of the multiple mutants were purified by the same procedures. All forms of aFGF, recombinant wild-type and the mutants were highly purified since only single 16 kDa bands were seen following reduction and electrophoresis in SDS 15% polyacrylamide gels at loads 100-fold above the threshold of detection.

EXAMPLE 8

Biological Activity of Mutated aFGF

Biological activity of the purified r-aFGF from Example 6 was evaluated using a fibroblast mitogenic assay modified from Thomas et al., J. Biol. Chem. 225: 5517-5520 (1980). BALB/c 3T3 A31 fibroblasts (American Type Culture Collection) were plated at $3 \times 10^4$ cells per 100 μl per well in 96-well culture dishes in culture media containing 10% heat-inactivated calf serum and incubated in 7% CO$_2$ (pH 7.35±0.05). The cells became fully quiescent by replacing the media with 1.0% heat-inactivated calf serum 6 and again 24 hours later. At 55 hours after plating, 10 μl of test sample with or without 5 μg of heparin and 0.11 μg of dexamethasone were added, at 70 hours each well was supplemented with 0.2 μCi of [methyl-$^3$H]-thymidine (20 Ci/mmole, New England Nuclear) and 0.3 μg of unlabeled thymidine (Sigma), and at 95 hours the cells were processed for determination of radiolabel incorporated into DNA. Each dose response point was the average of four determinations. The results of Ser-117 Mutant, the only mutant form showing activity equal to or greater than wild type, are shown in the following table:

TABLE XII

Mitogenic Responses of BALB/c 3T3 Fibroblasts to Mutated aFGF

| Dose | Wild type | | Ser-117 Mutant | |
|---|---|---|---|---|
| (amt/ml) | −heparin | +heparin | −heparin | +heparin |
| 3.16 pg | 1449 | 724 | 2055 | 883 |
| 10.0 pg | 1917 | 914 | 2662 | 1255 |
| 31.6 pg | 1547 | 1007 | 3076 | 2748 |
| 100 pg | 2263 | 2498 | 4833 | 8067 |
| 316 pg | 2647 | 14945 | 11505 | 44193 |
| 1.00 ng | 3975 | 54516 | 22869 | 66778 |
| 3.16 ng | 6400 | 68447 | 40487 | 60306 |
| 10.0 ng | 12665 | 61294 | 54163 | 56326 |
| 31.6 ng | 21843 | 56552 | 70670 | 59854 |
| 100 ng | 44744 | 66816 | 66802 | 63856 |

The 4 titration curves are compared at their half-maximal rise. The WT in the absence of heparin does not reach a peak so the same peak magnitude is assumed as seen for the other 3 peaks and the half-maximal value extrapolated.

TABLE XIII

Comparison of Concentrations Necessary for Half Maximal Stimulation

| Sample | Heparin | Conc. of ½ maximal stimulation |
|---|---|---|
| WT | − | 66 ng/ml |
|  | + | 0.56 ng/ml |
| Ser-117 | − | 2.3 ng/ml |
| Mutant | + | 0.20 ng/ml |

All dilutions were prepared from a stock solution containing 1.51 mg/ml of purified reactants. The Ser-117 mutant is at least as active as the wild type in the presence of heparin. The activity of the wild type is about 10-fold more dependent on heparin than the mutant consequently 90% of the heparin dependence of WT aFGF is eliminated in the Ser-117 mutant.

The mitogenic assay used to evaluate biological activity was modified so that mutated and wild-type aFGF could be compared. Heat-inactivated calf serum was replaced with 1% insulin-selenium-transferin (ITS), 0.4 gm L histidine, 50 μl of 1M ethanolamine, 1.25 gm bovine serum albumin with 5.35 mg of linoleic acid per liter of 75% DMED, 25% Ham's F12 containing both penicillin-streptomycin and L-glutamine as described above. Full dose-response assays were done as described above at consecutive two-fold dilutions over at least 3 log orders of aFGF concentration spanning the complete rise of the response from background through peak DNA synthesis levels. All concentration points were done in quadruplicate on confluent Balb/c 3T3 cells in 96 well dishes. One stimulatory unit was calculated as the amount of aFGF per ml that generated a half-maximal response. The specific mitogenic activity is the number of such stimulatory units per mg of pure aFGF. All samples of aFGF were prediluted to 50 μg/ml in the same TFA/CH$_3$CN solvent. The activities of wild-type and mutated aFGF are compared in the following table.

TABLE XIV

| Sample | With Heparin | Without Heparin | Fold Increase |
|---|---|---|---|
| WT | 5.37 ng/ml (0.186 × 10$^6$) | 269 pg/ml (3.72 × 10$^6$) | 20.0 |
| Ser 16 | 33.9 ng/ml (0.030 × 10$^6$) | 400 pg/ml (2.50 × 10$^6$) | 84.8 |
| Ser 83 | 4.36 ng/ml (0.229 × 10$^6$) | 251 pg/ml (3.98 × 10$^6$) | 17.4 |
| Ser 117 | 182 ng/ml (0.549 × 10$^6$) | 240 pg/ml (4.17 × 10$^6$) | 7.58 |
| Ser 16,83 | 800 pg/ml (1.25 × 10$^6$) | 195 pg/ml (5.13 × 10$^6$) | 4.10 |
| Ser 16,117 | 741 pg/ml (1.35 × 10$^6$) | 148 pg/ml (6.76 × 10$^6$) | 5.01 |
| Ser 83,117 | 295 pg/ml (3.39 × 10$^6$) | 100 pg/ml (10.0 × 10$^6$) | 2.95 |
| Ser 16,83,117 | 427 pg/ml (2.34 × 10$^6$) | 107 pg/ml (9.35 × 10$^6$) | 3.99 |

Figure 2B:
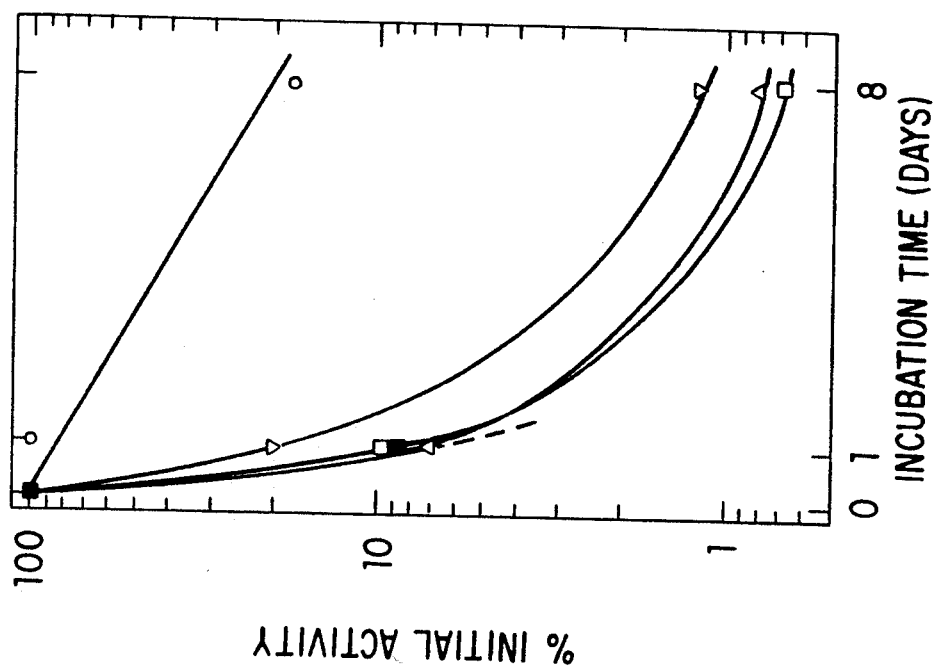
FIG. 2(A) and (B) demonstrate the stability of recombinant wild type haFGF and mutant haFGF measuring mitogenic activity versus time in the presence of heparin (A) and absence of heparin (B).
Figure 2A:
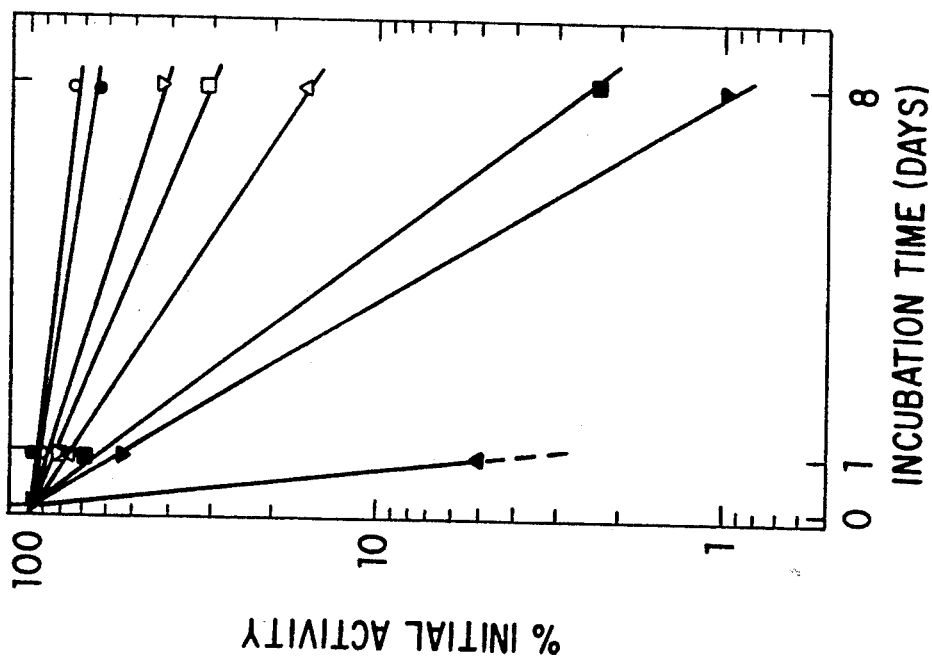

The relative stabilities of the recombinant wild-type haFGF, the single Ser mutants and the multiple Ser mutants were determined. Mitogenic activities were measured following 0, 1 and 8 day incubations in serum-free DME solutions, normally used for serial sample dilutions, that were CO$_2$-buffered to pH 7.3 at 37° C. containing 1 mg/ml human serum albumin. Mitogen samples were stored at 512 ng/ml, with or without 500 μg heparin/ml, equivalent to the 10-fold concentrates from which the highest concentration point in the assay is diluted. Each sample was stored and assayed either in the presence or absence of heparin. The relative stabilities, following scaling to set each day 0 activity to 100%, are shown in FIG. 2 as a function of storage time. In FIG. 2: ▼ corresponds to wild type; ▲ corresponds to haFGF (Ser 16); ■ corresponds to haFGF (Ser (83); ● corresponds to haFGF (Ser (117); Δ corresponds to haFGF (Ser 16,83); △ corresponds to haFGF (Ser 16,117); □0 corresponds to haFGF (Ser 83,117); and ○ corresponds to haFGF (Ser 16,83,117).

The loss of activity of wild-type haFGF and the mutants in the presence of heparin closely fits an exponential decay, see FIG. 4A. The activities of all the mutants except Ser (16) are more stable than the wild-type mitogen. The most stable mutants, in descending order of stability are Ser 16,83,117), Ser (117) Ser (16,83), Ser (83,117), Ser (16,83) and Ser (83), Ser (16). The stability of Ser (83) was only slightly higher than the wild-type. The various forms of aFGF were less stable in the absence of heparin and with the apparent exception of Ser (16,83,117), the decay appeared not to be a simple exponential of the time period.

A sample of the expression vector pKK-haFGF(Ser 117) designated A48-1al containing the gene capable of expressing the serine 117 mutant in *E. coli* DH5 was deposited in the American Type Culture Collection, 12301 Parklawn Drive, Rockville, Md. 20852 USA, on Sep. 30, 1987 under the Budapest Treaty and has been assigned ATCC number 67522.

What is claimed is:

1. Recombinant human mutant, biologically active, microheterogeneous forms of acidic fibroblast growth factor wherein all three cysteine residues at positions 16, 83, and 117, numbered in accordance with the native human 140 amino acid microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

2. The recombinant human mutant microheterogeneous forms of acidic fibroblast growth factor of claim 1 wherein the mutant acidic fibroblast growth factor is of the 154, 140 or 139 amino acid microheterogeneous form.

3. The recombinant human mutant microheterogeneous forms of acidic fibroblast growth factor of claim 1 wherein said amino acid incapable of forming intramolecular or intermolecular disulfide bonds is serine.

4. Recombinant human mutant, biologically active, microheterogeneous forms of acidic fibroblast growth factor wherein any two or more of the cysteine residues at positions 16, 83 and 117, numbered in accordance with the native human 140 amino acid microheterogeneous form, are replaced with an amino acid incapable of forming intramolecular or intermolecular disulfide bonds, wherein said mutant acidic fibroblast growth factor has increased biological activity and less dependence on heparin when compared to native acidic fibroblast growth factor and optionally having an additional methionine attached to the N-terminus of said microheterogeneous forms.

5. The recombinant human mutant microheterogeneous forms of acidic fibroblast growth factor of claim 4 wherein the mutant acidic fibroblast growth factor is of the 154, 140 or 139 amino acid microheterogeneous form.

6. The recombinant human mutant microheterogeneous forms of acidic fibroblast growth factor of claim 4 wherein said amino acid incapable of forming intramolecular or intermolecular disulfide bonds is serine.

7. Recombinant human mutant, biologically active, microheterogeneous forms of acidic fibroblast growth factor wherein the cysteine at position 117, numbered in accordance with the native human 140 amino acid microheterogeneous form, is replaced with an amino acid incapable of forming intramolecular or intermolecular disulfide bonds, and optionally having an additional methionine attached to the N-terminus and wherein said mutant acidic fibroblast growth factor has greater biological activity in the absence of heparin than the native human acidic fibroblast growth factor.

8. The recombinant human mutant microheterogeneous forms of acidic fibroblast growth factor of claim 7 wherein the mutant acidic fibroblast growth factor is of the 154, 140 or 139 amino acid microheterogeneous form.

9. The recombinant human mutant microheterogeneous forms of acidic fibroblast growth factor of claim 7 wherein said amino acid incapable of forming intramolecular or intermolecular disulfide bonds is serine.

10. The recombinant human mutant, biologically active, microheterogeneous forms of acidic fibroblast growth factor of claims 1, 4 or 7 wherein the methionine residue at position 67, numbered in accordance with the native human 140 amino acid microheterogeneous form, is replaced by a non-air-oxidizable amino acid and optionally having an additional methionine attached to the N-terminus of said microheterogeneous forms wherein said mutant acid fibroblast growth factor has greater biological activity in the absence of heparin than the native human acidic fibroblast growth factor.

11. The recombinant human mutant microheterogeneous forms of acidic fibroblast growth factor of claim 10 wherein the non-air-oxidizable amino acid is either alanine, valine, leucine or isoleucine.

12. The recombinant human mutant microheterogeneous forms of acidic fibroblast growth factor of claim 10 wherein the non-air-oxidizable amino acid is leucine.

13. A pharmaceutical composition for comprising a pharmaceutical carrier and an effective amount to promote tissue repair of the recombinant human mutant microheterogeneous acidic fibroblast growth factor of claim 1.

14. A pharmaceutical composition for comprising a pharmaceutical carrier and an effective amount to promote tissue repair of the recombinant human mutant microheterogeneous acidic fibroblast growth factor of claim 4.

15. A pharmaceutical composition comprising a pharmaceutical carrier and an effective amount to promote tissue repair of the recombinant human mutant microheterogeneous acidic fibroblast growth factor of claim 7.

16. A pharmaceutical composition comprising a pharmaceutical carrier and an effective amount to promote tissue repair of the recombinant human mutant microheterogeneous acidic fibroblast growth factor of claim 10.

17. A recombinant human mutant, biologically active, acidic fibroblast growth factor having the following amino acid sequence:

```
       -14                -10                                              -1  1
       Ala—Glu—Gly—Glu—Ile—Thr—Thr—Phe—Thr—Ala—Leu—Thr—Glu—Lys—Phe—Asn—Leu—Pro—

10                                            20
       Pro—Gly—Asn—Tyr—Lys—Lys—Pro—Lys—Leu—Leu—Tyr—Cys—Ser—Asn—Gly—Gly—His—Phe—

30                                            40
       Leu—Arg—Ile—Leu—Pro—Asp—Gly—Thr—Val—Asp—Gly—Thr—Arg—Asp—Arg—Ser—Asp—Gln—

50
       His—Ile—Gln—Leu—Gln—Leu—Ser—Ala—Glu—Ser—Val—Gly—Glu—Val—Tyr—Ile—Lys—Ser—Thr—

60                                      70
       Glu—Thr—Gly—Gln—Tyr—Leu—Ala—Met—Asp—Thr—Asp—Gly—Leu—Leu—Tyr—Gly—Ser—Gln—

80                                      90
       Thr—Pro—Asn—Glu—Glu—Cys—Leu—Phe—Leu—Glu—Arg—Leu—Glu—Glu—Asn—His—Tyr—Asn—
```

```
                          100                                               110
Thr—Tyr—Ile—Ser—Lys—Lys—His—Ala—Glu—Lys—Asn—Trp—Phe—Val—Gly—Leu—Lys—Lys—

120                                               130
Asn—Gly—Ser—Ser—Lys—Arg—Gly—Pro—Arg—Thr—His—Tyr—Gly—Gln—Lys—Ala—Ile—Leu—

140
Phe—Leu—Pro—Leu—Pro—Val—Ser—Ser—Asp
``` and all microheterogeneous forms thereof optionally having an additional methionine attached to the N-terminus of said microheterogeneous form.

18. The recombinant human mutant microheterogeneous acidic fibroblast growth factor of claim 17 wherein the methionine residue at position 67 is replaced by leucine.

19. A recombinant human mutant, biologically active, acidic fibroblast growth factor having the following amino acid sequence:

```
-14                  -10                                        -1   1
Ala—Glu—Gly—Glu—Ile—Thr—Thr—Phe—Thr—Ala—Leu—Thr—Glu—Lys—Phe—Asn—Leu—Pro—

10                                              20
Pro—Gly—Asn—Tyr—Lys—Lys—Pro—Lys—Leu—Leu—Tyr—Cys—Ser—Asn—Gly—Gly—His—Phe—

30                                           40
Leu—Arg—Ile—Leu—Pro—Asp—Gly—Thr—Val—Asp—Gly—Thr—Arg—Asp—Arg—Ser—Asp—Gln—

50
His—Ile—Gln—Leu—Gln—Leu—Ser—Ala—Glu—Ser—Val—Gly—Glu—Val—Tyr—Ile—Lys—Ser—Thr—

60                                          70
Glu—Thr—Gly—Gln—Tyr—Leu—Ala—Met—Asp—Thr—Asp—Gly—Leu—Leu—Tyr—Gly—Ser—Gln—

80                                              90
Thr—Pro—Asn—Glu—Glu—Ser—Leu—Phe—Leu—Glu—Arg—Leu—Glu—Glu—Asn—His—Tyr—Asn—

100                                               110
Thr—Tyr—Ile—Ser—Lys—Lys—His—Ala—Glu—Lys—Asn—Trp—Phe—Val—Gly—Leu—Lys—Lys—

120                                               130
Asn—Gly—Ser—Ser—Lys—Arg—Gly—Pro—Arg—Thr—His—Tyr—Gly—Gln—Lys—Ala—Ile—Leu—

140
Phe—Leu—Pro—Leu—Pro—Val—Ser—Ser—Asp
``` and all microheterogeneous forms thereof optionally having an additional methionine attached to the N-terminus of said microheterogeneous form.

20. The recombinant human mutant microheterogeneous acidic fibroblast growth factor of claim 19 wherein the methionine residue at position 67 is replaced by leucine.

21. A recombinant human mutant, biologically active, acidic fibroblast growth factor having the following amino acid sequence:

```
-14                  -10                                        -1   1
Ala—Glu—Gly—Glu—Ile—Thr—Thr—Phe—Thr—Ala—Leu—Thr—Glu—Lys—Phe—Asn—Leu—Pro—

10                                              20
Pro—Gly—Asn—Tyr—Lys—Lys—Pro—Lys—Leu—Leu—Tyr—Ser—Ser—Asn—Gly—Gly—His—Phe—

30                                           40
Leu—Arg—Ile—Leu—Pro—Asp—Gly—Thr—Val—Asp—Gly—Thr—Arg—Asp—Arg—Ser—Asp—Gln—

50
His—Ile—Gln—Leu—Gln—Leu—Ser—Ala—Glu—Ser—Val—Gly—Glu—Val—Tyr—Ile—Lys—Ser—Thr—

60                                          70
Glu—Thr—Gly—Gln—Tyr—Leu—Ala—Met—Asp—Thr—Asp—Gly—Leu—Leu—Tyr—Gly—Ser—Gln—

80                                              90
Thr—Pro—Asn—Glu—Glu—Ser—Leu—Phe—Leu—Glu—Arg—Leu—Glu—Glu—Asn—His—Tyr—Asn—

100                                               110
Thr—Tyr—Ile—Ser—Lys—Lys—His—Ala—Glu—Lys—Asn—Trp—Phe—Val—Gly—Leu—Lys—Lys—

120                                               130
Asn—Gly—Ser—Ser—Lys—Arg—Gly—Pro—Arg—Thr—His—Tyr—Gly—Gln—Lys—Ala—Ile—Leu—

140
Phe—Leu—Pro—Leu—Pro—Val—Ser—Ser—Asp
``` and all microheterogeneous forms thereof optionally having an additional methionine attached to the N-terminus of said microheterogeneous form.

22. The recombinant human mutant microheterogeneous acidic fibroblast growth factor of claim 21 wherein the methionine residue at position 67 is replaced by leucine.

* * * * *